United States Patent
Lamb

(10) Patent No.: US 12,263,198 B1
(45) Date of Patent: Apr. 1, 2025

(54) COMPOSITIONS AND METHODS OF IMPROVING RUMINANT PERFORMANCE

(71) Applicant: Ralco Nutrition, Inc., Marshall, MN (US)

(72) Inventor: Richard Dale Lamb, Balaton, MN (US)

(73) Assignee: Ralco Nutrition, Inc., Marshall, MN (US)

( * ) Notice: Subject to any disclaimer, the term of this patent is extended or adjusted under 35 U.S.C. 154(b) by 40 days.

(21) Appl. No.: 17/576,733

(22) Filed: Jan. 14, 2022

Related U.S. Application Data

(60) Provisional application No. 63/137,992, filed on Jan. 15, 2021.

(51) Int. Cl.

| | |
|---|---|
| *A61K 36/062* | (2006.01) |
| *A23K 10/16* | (2016.01) |
| *A23K 10/30* | (2016.01) |
| *A23K 20/105* | (2016.01) |
| *A23K 20/158* | (2016.01) |
| *A23K 20/163* | (2016.01) |
| *A23K 50/10* | (2016.01) |
| *A61K 33/24* | (2019.01) |
| *A61K 47/36* | (2006.01) |

(52) U.S. Cl.
CPC ............ *A61K 36/062* (2013.01); *A23K 10/16* (2016.05); *A23K 10/30* (2016.05); *A23K 20/105* (2016.05); *A23K 20/158* (2016.05); *A23K 20/163* (2016.05); *A23K 50/10* (2016.05); *A61K 33/24* (2013.01); *A61K 47/36* (2013.01)

(58) Field of Classification Search
CPC ...... A61K 36/062; A61K 33/24; A61K 47/36; A23K 10/16; A23K 10/30; A23K 20/105; A23K 20/158; A23K 20/163; A23K 50/10
See application file for complete search history.

(56) References Cited

U.S. PATENT DOCUMENTS

| | | |
|---|---|---|
| 9,241,502 B2 | 1/2016 | Block et al. |
| 10,143,218 B1 | 12/2018 | Downs et al. |
| 10,835,561 B2 | 11/2020 | Rehberger et al. |
| 2006/0188549 A1 | 8/2006 | Block et al. |
| 2008/0020095 A1 | 1/2008 | Block et al. |
| 2010/0178300 A1 | 7/2010 | Yiannikouris et al. |
| 2011/0152363 A1 | 6/2011 | Knochenmus et al. |
| 2012/0135112 A1 | 5/2012 | Hiolle et al. |
| 2015/0297632 A1 | 10/2015 | Auclair et al. |
| 2016/0206654 A1 | 7/2016 | Sandberg |
| 2018/0070612 A1 | 3/2018 | Wan et al. |
| 2018/0125913 A1* | 5/2018 | Lamb ............... A23L 33/105 |
| 2019/0124949 A1 | 5/2019 | Ghalamkari et al. |
| 2019/0209637 A1 | 7/2019 | Lamb |
| 2021/0015120 A1 | 1/2021 | Lamb |

FOREIGN PATENT DOCUMENTS

| | | |
|---|---|---|
| CA | 3133602 A1 | 11/2016 |
| WO | 200221930 A1 | 3/2002 |

OTHER PUBLICATIONS

Kuester, Olivia Jayne, Thesis, "An Evaluation of Feeding a Blend of Essential Oils and Cobalt Lactate to Lactating Dairy Cows" (2016). Electronic Theses and Dissertations. 1051. https://openprairie.sdstate.edu/etd/1051. (Year: 2016).*

Emprove MX—Emmert, retrieved from https://www.emmert.com/emmert-livestock/emprove-mx-brewers-yeast-ingredients/, on Mar. 16, 2021.

Ghazanfar, S., Khalid, N., & Imran, I. A. a. (2017). Probiotic Yeast: Mode of Action and Its Effects on Ruminant Nutrition. In A. Morata, & I. Loira (Eds.), Yeast—Industrial Applications. IntechOpen. https://doi.org/10.5772/intechopen.70778.

"Translation of 2002/21930 A1 PCT reference", Mar. 21, 2002.

Marston, "The many benefits of adding yeast cultures to creep feeds", Retrieved from https://www.hubbardfeeds.com/blog/many-benefits-adding-yeast-cultures-creep-feeds on Mar. 16, 2021.

PCT/US2020/042404, "International Search Report and Written Opinion", Dec. 3, 2020.

Robinson, "Yeast Products for Growing and Lactating Ruminants: A Literature Summary of Impacts on Rumen Fermentation and Performance", Cooperative Extension University of California, Davis , 2022.

Overton, "Ways to Manage Trace Minerals in Dairy Rations", https://www.agproud.com/articles/22633-ways-to-manage-trace-minerals-in-dairy-rations (Year: 2014), Aug. 2014, 38.

"Essential oil chemistry of the genus *Thymus*—a global view", 2002, 34 Pages.

Baldan, et al., "Larix decidua Bark as a Source of Phytoconstituents: An LC-MS Study", https://doi.org/10.3390/molecules22111974 (Year:2017), 2017, 14 Pages.

Kuester, "An Evaluation of Feeding a Blend of Essential Oils and Cobalt Lactate to Lactating Dairy Cows", South Dakota State University. Electronic Theses and Dissertations. 1051. https://openprairie.sdstate.edu/etd/ 1051, 2016, 71 Pages.

(Continued)

*Primary Examiner* — Kade Ariani

(74) *Attorney, Agent, or Firm* — Merchant & Gould P.C.

(57) ABSTRACT

Embodiments include feed additive compositions for improving performance of a ruminant, methods of improving performance of a ruminant, and the like. The feed additive compositions for improving performance of a ruminant may include a blend of a cobalt compound and a yeast component. In some examples, the blend may further include an essential oil composition. The methods for improving performance of a ruminant may include administering to a ruminant a daily dose of the feed additive composition containing between about 3 and about 10 grams of the yeast component, and between about 75 and about 225 milligrams of the cobalt compound. The feed composition may perform at least one of the following: increase milk production of dairy cows, increase feed efficiency, increase digestibility, and improve early rumen development.

11 Claims, 16 Drawing Sheets

(56) References Cited

OTHER PUBLICATIONS

Pretz, "Improving Feed Efficiency through Forage Strategies for Increasing Dairy Profitability and Sustainability.", ProQuest Dissertations Publishing, 2016. (Year: 2016), 2016, 121 Pages.

* cited by examiner

Study conducted by J.P. Pretz, J.W. Wu, M. Jao, B. Halloway, D. Davis and D.P. Casper at South Dakota State University

COMPOSITIONS AND METHODS OF IMPROVING RUMINANT PERFORMANCE

BACKGROUND

A need exists for compositions for improving the performance of ruminants.

SUMMARY

According to one aspect of the invention, a method of improving performance of a ruminant is provided. The method of improving performance of a ruminant may include administering to a ruminant an amount of a feed additive composition sufficient to increase milk production, improve digestion, improve early rumen development, and increase nutrient intake leading to increased growth, wherein the feed additive composition includes at least one of the following: a cobalt compound, a yeast component, and an essential oil composition. In some embodiments, the feed additive composition includes the cobalt compound and the yeast component in combination. In some embodiments, the feed additive composition includes the three components (cobalt, yeast and essential oil) in combination.

According to another aspect of the invention, a feed additive composition for improving performance of a ruminant is provided. The feed additive composition for improving performance of a ruminant may include at least one of the following: a cobalt compound, a yeast component, and an essential oil composition.

According to a further aspect of the invention, a method of preparing a feed composition for improving performance of a ruminant is provided. The method of preparing a feed composition for improving performance of a ruminant may include applying a feed additive composition to animal feed, wherein the feed additive composition includes at least one of the following: a cobalt compound, a yeast component, and an essential oil composition.

This summary is intended to provide an overview of subject matter of the present disclosure. It is not intended to provide an exclusive or exhaustive explanation of the invention. The detailed description is included to provide further information about the present patent application.

BRIEF DESCRIPTION OF THE DRAWINGS

In the drawings, which are not necessarily, drawn to scale, like numerals may describe similar components in different views. The drawings illustrate generally, by way of example, but not by way of limitation, various embodiments discussed herein.

DETAILED DESCRIPTION

Discussion

Figure 1:
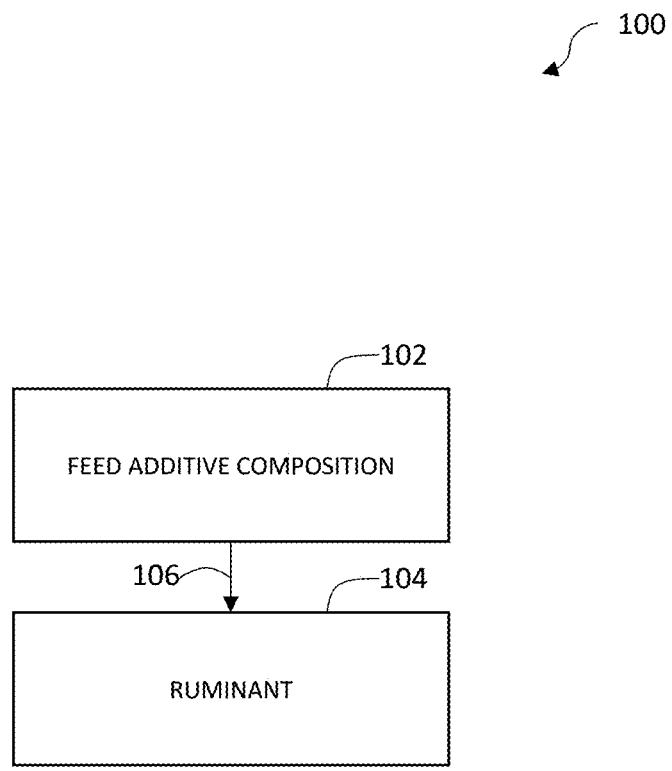
FIG. 1 is a flowchart of a method of improving performance of a ruminant, according to one or more embodiments of the present disclosure.

The present invention provides feed additive compositions and related methods for improving one or more of the health, growth, and performance of ruminants. As described herein, it has been unexpectedly discovered that feed additive compositions including one or more of a cobalt compound, a yeast component, and an essential oil composition yields synergistic beneficial results when administered to ruminants. More specifically, it has been discovered that administering the feed additive compositions to ruminants may improve the performance of said ruminants. The feed additive composition can include a combination of the cobalt compound and the yeast component. In other examples, the feed additive composition can include a combination of all three components-yeast, cobalt and essential oil. The improvements in performance may include, for example and without limitation, one or more of the following: stimulating native rumen microbes to increase enzyme production (e.g., for fiber digestion), while also selectively targeting the growth of beneficial microbes, including microbes involved in the production of enzymes: increasing the production and/or rate of production of at least one volatile fatty acid in the rumen: decreasing the production and/or rate of production of methane: increasing the digestion and/or rate of digestion by the ruminant; and decreasing a concentration of ammonia in the rumen.

These improvements may correlate to significant and/or marked improvements in one or more of the following: increased feed intake, increased feed efficiency, increased fiber digestibility, increased digestion, higher average daily gains, improved reproduction and weaning weights, healthier body conditions, and increased milk production in dairy cows. For example, administering the feed additive compositions of the present disclosure to ruminants may achieve one or more of the following improvements: an increase in feed intake, an increase in feed digestion, an increase in average daily gain, an improvement in reproduction and weaning weights, a healthier body condition, and an increase in milk production in dairy cows. The feed additive compositions of the present disclosure may be administered to support optimal rumen performance, enhance fiber digestibility for maximum volatile fatty acid (VFA) production which is the energy required for improved growth and performance, support gut health and gut immune function for improved health, and improve gains, milk production, and reproduction, among other things.

The examples in the Examples section below show that a treatment of a feed additive composition comprising cobalt lactate and yeast resulted in numerous benefits, including increased milk production, higher digestibility, early rumen development (as evidenced by increased ruminal bacteria and protozoa), early ability to digest fiber, and greater nutrient intake, enabling increased growth. The calf trial showed that the treatment enabled the calves to eat more hay, allowing for more forage in the ration to reduce feed costs.

Embodiments of the present disclosure provide feed additive compositions for improving the performance of ruminants. In some embodiments, the improvements in performance include at least one of the following: an increase in production of at least one enzyme in the rumen, an increase in production of at least one volatile fatty acid in the rumen, and/or a decrease in production of methane in the rumen. The feed additive compositions may include one or more of a cobalt compound, a yeast component, and an essential oil composition. Any combination of the cobalt compound, the yeast component, and/or the essential oil composition may be included in the feed additive compositions. For example, in some embodiments, the feed additive compositions include at least the cobalt compound and the yeast component. In some embodiments, the feed additive compositions include the cobalt compound, the yeast component, and the essential oil compositions. Other combinations are possible and thus the foregoing shall not be limiting.

The feed additive compositions may be provided in solid form, liquid form, or mixtures thereof (e.g., slurry form). In some embodiments, the feed additive compositions are provided in liquid or concentrated liquid form, solid form, or soluble concentrated powder form. In some embodiments, the feed additive compositions are provided as a solid or solid mixture, liquid or liquid mixture, or solid-liquid mixture. In some embodiments, the feed additive compositions may be provided in liquid form, as a liquid. The feed compositions may be provided as suspensions, colloidal dispersions, slurries, emulsions, and the like. The feed compositions may be wet or dry (e.g., include or exclude moisture). In some embodiments, the feed additive composition is provided in a powder form, a pellet form, a solution form, or a concentrated solution form.

Suitable cobalt compounds include cobalt chelates, cobalt salts, and hydrates thereof (e.g., tetrahydrates, pentahydrates, hexahydrates, heptahydrates, octahydrates, nonahydrates, etc.), with preference given to water-soluble cobalt compounds. Examples of suitable cobalt compounds include, without limitation, one or more of a cobalt lactate compound, a cobalt acetate compound, a cobalt formate compound, a cobalt oxalate compound, a cobalt propionate compound, a cobalt butyrate compound, a cobalt gluconate compound, a cobalt fumarate compound, a cobalt valerate compound, a cobalt 2-ethylcaproate compound, a cobalt citrate compound, a cobalt sorbate compound, a cobalt benzoate compound, a cobalt enanthate compound, a cobalt dioctanoate compound, a cobalt pelargonate compound, a cobalt decanoate compound, a cobalt laurate compound, a cobalt myristate compound, a cobalt palmitate compound, a cobalt margarate compound, a cobalt stearate compound, a cobalt icosanoate compound, a cobalt ethylenediamine tetraacetate (EDTA) compound, a cobalt ethylene diamine compound, a cobalt bromide compound, a cobalt chloride compound, a cobalt fluoride compound, a cobalt carbonate compound, a cobalt hydroxide compound, a cobalt nitrate compound, a cobalt oxide compound, a cobalt phosphate compound, a cobalt sulfate compound, a cobalt malate compound, a cobalt tartrate compound, and any hydrate thereof. Exemplary cobalt compounds include cobalt lactate compounds, such as for example cobalt lactate, and cobalt acetate compounds, such as for example cobalt (II) acetate tetrahydrate.

In some embodiments, the cobalt compound is cobalt lactate, and the amount of cobalt lactate is between about 1 and about 3 percent (by weight) of the feed additive composition, between about 1.15 and about 2.5 percent, and between about 1.15 and about 2.3 percent. In some embodiments, the amount of cobalt lactate given to the ruminant is between about 75 and about 225 milligrams per head per day, between about 75 and about 150 milligrams per head per day. The amount of cobalt lactate given depends, in part, on a feeding rate. The amount (by weight) of cobalt in cobalt lactate is about 20 percent. The composition of the feed additive can also be described in terms of the amount of cobalt, rather than the amount of cobalt lactate. In some embodiments, the amount of cobalt given to the ruminant is between about 15 and about 45 milligrams per head per day, between about 15 and about 30 milligrams per head per day. In an example, the cobalt lactate is Microbial Catalyst® from Ralco.

The yeast component may include one or more of a yeast, a yeast culture, a concentrated yeast culture, a yeast extract, a yeast product, a fermented yeast, and a modified form of any thereof. A yeast may include a yeast organism (e.g., a yeast species). A yeast culture may include a cultivated growth of a yeast organism. A yeast extract may include cell contents of a yeast without cell walls. A yeast product may include one or more products produced directly or indirectly by yeast through fermentation. Examples include, without limitation, one or more of metabolites, amino acids, vitamins, enzymes, and minerals. A fermented yeast may include a yeast and its products. A modified form includes any of the foregoing including a yeast which has been modified in some manner.

Examples of suitable yeasts include, but are not limited to, those belonging to thegenera: *Metschnikowia*, Aureobasidiuim, *Cryptococcus, Candida, Hanseniaspora, Pichia, Sporobolomyces, Sporidiobolus, Bulgaria, Cystofilobasidium, Malassezia, Saccharomyces, Rhodotorula, Mrakia, Glaciozyma, Starmerella, Wickerhamomyces, Tilletiopsis, Galactomyces, Issatchenkia, Kluyveromyces, Bensingtonia, Derxomyces, Hannaella, Dioszegia, Debaryomyces, Torulaspora, Trichosporon, Arthroderma, Hortaea, Rhodosporidium, Dipodascopsis, Kazachstania*, and *Kockovaella*.

Examples of suitable species of yeasts include, but are not limited to, one or more of *Saccharomyces cerevisiae, Saccharomyces chevaiieri, Saccharomyces delbrueckii, Saccharomyces exiguus, Saccharomyces fermentati, Saccharomyces logos, Saccharomyces mellis, Saccharomyces microellipsoides, Saccharomyces oviformis, Saccharomyces rosei, Saccharomyces rouxii, Saccharomyces sake, Saccharomyces uvarum* Beij'er, *Saccharomyces willianus, Saccharomyces* sp., *Saccharomyces ludwigii, Saccharomyces sinenses, Saccharomyces bailii, Saccharomyces carlsbergensis, Schizosaccharomyces octosporus, Schizosaccharomyces pombe, Sporobolomyces roseus, Sporobolomyces salmonicolor, Torulopsis Candida, Torulopsis famta, Torulopsis globosa, Torulopsis inconspicua, Trichosporon behrendoo, Trichosporon capitatum, Trichosporon cutaneum, Wickerhamia* fluoresens, *Ashbya gossypii, Blastomyces dermatitidis, Candida albicans, Candida arborea, Candida guillermondii, Candida Krusei, Candida* lambxca, *Candida lipolytica, Candida* par akrusei, *Candida* par apsilosis, *Candida* par apsilosis, *Candida pseudotropicalis, Candida pulcherrima, Candida robusta, Candida rugousa, Candida utilis, Citeromyces matritensis, Crebrothecium* ashbyii, *Cryptococcus laurentii, Cryptococcus neoformans, Debaryomyces hansenii, Debaryomyces kloeckeri, Endomycopsis fibuligera, Eremothecium* ashbyii, *Geotrichum candidum, Geotrichum ludwigii, Geotrichum robustum, Geotrichum suaveolens, Hansenula anomala, Hansenula arabitolgens, Hansenula jadinii, Hansenula saturnus, Hansenula schneggii, Hansenula subpelliculosa, Kloeckera apiculata, Lipomyces starkeyi, Pichia* far inosa, *Pichia membranaefaciens, Rhodosporidium toruloides, Rhodotorula aurantiaca, Rhodotorula glutinis, Rhodotorula minuta, Rhodotorula rubar*, and *Rhodotorula sinesis*.

The yeast component may include or be combined with one or more vitamins and one or more cofactors. A cofactor may include a metal ion cofactor, a coenzyme, and/or a coenzyme precursor. In an embodiment, the yeast component may include a mixture of one or more of amino acids, peptides, water-soluble vitamins, and carbohydrates. For example, in some embodiments, the yeast component may include compounds of one or more of thiamin, riboflavin, niacin, biotin, vitamin B6, folic acid, panthenol, pantothenic acid, inositol, cyanocobalamin, citric acid, pyridoxine, calcium, copper, selenium, iron, magnesium, manganese, phosphorous, potassium, sodium, and zinc. In embodiments in which the yeast component includes or is combined with one or more vitamins and one or more cofactors, the yeast component may be referred to as vitamin-enriched yeast extract. For example, in an embodiment, the yeast component is a vitamin-enriched yeast component.

The listed vitamins and cofactors can be provided in the composition in any form including vitamin derivatives and provitamin forms. Optionally, one or more alcohols can be utilized in the composition to enhance the activity and aid in the preservation of one or more vitamins. In an embodiment, an alcohol that may be utilized is benzyl alcohol.

The thiamine compounds may include one or more of thiamine hydrochloride, thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine triphosphoric acid ester, and thiamine triphosphoric acid salt.

The riboflavin compounds may include one or more of riboflavin, riboflavin acetyl phosphate, flavin adenine dinucleotide, flavin adenine mononucleotide, and riboflavin phosphate.

The niacin compounds may include one or more of niacinamide, nicotinic acid, nicotinic acid adenine dinucleotide, nicotinic acid amide, nicotinic acid benzyl ester, nicotinic acid monoethanolamine salt, nicotinic acid hydrazide, nicotinic acid hydroxyamate, nicotinic acid-N-(hydroxymethyl)amide, nicotinic acid methyl ester, nicotinic acid mononucleotide, and nicotinic acid nitrite.

The pyridoxine compounds may include one or more of pyridoxine hydrochloride, and pyridoxal phosphate. Suitable forms of folic acid compounds may include one or more of folic acid and folinic acid.

The biotin compounds may include one or more of biotin, biotin sulfoxide, yeast, yeast extract, biotin 4-amidobenzoic acid, biotin amidocaproate N-hydroxysuccinimide ester, biotinyl 6-aminoquinoline, biotin hydrazide, biotin methyl ester, d-biotin-N-hydroxysuccinimide ester, biotin-maleimide, d-biotin p-nitrophenyl ester, biotin propranolol, 5-(N-biotinyl)-3-aminoallyl)-uridine 5'-triphosphate, biotinylated urddine 5'-triphosphate, and N-e-biotinyl-lysine.

The panthothenic acid compounds may include one or more of coenzyme A.

In an embodiment, the yeast component includes one or more of sulfur, phosphorus, potassium, magnesium, calcium sodium, iron, manganese, copper, zinc, selenium, aspartic acid, threonine, serine, glutamic acid, proline, glycine, alanine, cysteine, valine, methionine, isoleucine, leucine, tyrosine, phenylalanine, lysine, histidine, arginine, tryptophan, nitrogen, and organic carbon.

In some embodiments, the amount of the yeast component in the feed additive composition is between about 48 and about 98 percent (by weight) of the feed additive composition, between about 85 and about 98 percent, between about 90 and about 98 percent, between about 94 and about 97, and between about 96 and about 97 percent. In some embodiments, the amount of yeast given to the ruminant is between about 3 and about 10 grams per head per day, between about 3 and about 7 grams per head per day, between about 6.5 and about 7 grams per head per day, between about 6.6 and about 6.8 grams per head per day, between about 6.7 and about 6.8 grams per head per day, between about 3 and about 3.5 grams per head per day, and between about 3.25 and 3.4 grams per head per day. In an example, the yeast component is Emprove MX from Emmert. In other examples, the yeast component can include, but is not limited to, Emprove 28, Diamond V XPC, Diamond V XPC Ultra, Clelmanax, and Levucell SC. It is recognized that some of the listed yeast products are similar but may vary in concentration.

In some embodiments, the feed additive composition, which can be a blend of the yeast component and the cobalt compound, can be given to the ruminant at a feeding rate of between about 3 and about 10 grams per head per day. In other embodiments, the feeding rate can be between about 3.5 and about 7 grams per head per day. The feeding rate or dose can depend, in part, on a size and weight of the ruminant.

As provided above, the amount of the yeast component and the amount of the cobalt compound in the feed additive composition can be quantified in terms of a daily amount (for example, in grams or milligrams) or in terms of a weight percent of the composition. The amounts of yeast and cobalt can also be defined as a ratio of one another, which can be independent of the feeding rate. In an example in which the cobalt compound is cobalt lactate, the ratio can be defined as yeast to cobalt lactate or yeast to cobalt (the portion, by weight, of the cobalt within the cobalt lactate).

In some embodiments, the ratio of yeast to cobalt lactate is between about 140:1 and 13:1, between about 95:1 and about 15:1, between about 50:1 and about 25:1, and between about 45:1 and 40:1. In some embodiments, the ratio of yeast to cobalt (not cobalt lactate) is between about 700:1 and about 65:1, between about 470:1 and about 65:1, between about 250:1 and about 140:1, and between about 230:1 and about 200:1.

The Examples section below includes feed additive compositions of blended formulations of yeast and cobalt lactate. In other examples, the feed additive composition of a yeast component and a cobalt compound can further comprise an essential oil composition.

The essential oil compositions may include at least one essential oil. The at least one essential oil may include at least one of a natural essential oil and a synthetic essential oil, such as a nature's equivalent essential oil. The at least one essential oil may be emulsified or may not be emulsified. The essential oil compositions may include any combination of the essential oils disclosed herein, or may include a single essential oil.

In some embodiments, the essential oil composition includes at least one of the following essential oils: cinnamon essential oil, thyme essential oil, oregano essential oil, *capsicum* essential oil, alfalfa essential oil, allspice essential oil, almond essential oil, ambrette essential oil, *angelica* root essential oil, *angelica* seed essential oil, *angelica* stem essential oil, angostura essential oil, anise essential oil, asafetida essential oil, balm essential oil, balsam of Peru essential oil, basic essential oil, bay leaves essential oil, bay (myrcia oil) essential oil, bergamot (bergamot orange) essential oil, bitter almond essential oil, bois de rose essential oil, cacao essential oil, chamomile flowers essential oil, *Cananga* essential oil, caraway essential oil, cardamom seed essential oil, carob bean essential oil, carrot essential oil, cascarilla bark essential oil, *cassia* bark essential oil, celery seed essential oil, cherry essential oil, chervil essential oil, chicory essential oil, citronella essential oil, citrus peels essential oil, clary essential oil, clove bud essential oil, clove leaf essential oil, clove stem essential oil, clover essential oil, coca essential oil, coffee essential oil, cola nut essential oil, coriander essential oil, corn silk essential oil, cumin essential oil, curacao orange peel essential oil, cusparia bark essential oil, dandelion essential oil, dandelion root essential oil, dill essential oil, dog grass essential oil, elder flowers essential oil, estragole essential oil, estragon essential oil, fennel essential oil, fenugreek essential oil, galanga essential oil, garlic essential oil, geranium essential oil, ginger essential oil, *glycyrrhiza* essential oil, glycyrrhizin essential oil, grapefruit essential oil, guava essential oil, hickory bark essential oil, horehound essential oil, hops essential oil, horsemint essential oil, hyssop essential oil, immortelle essential oil, jasmine essential oil, juniper essential oil, kola nut essential oil, laurel berries essential oil, laurel leaves essential oil, lavender essential oil, lavandin essential oil, lemon essential oil, lemon grass essential oil, lemon peel essential oil, licorice essential oil, lime essential oil, linden flowers essential oil, locust bean essential oil, lupulin essential oil, mace essential oil, malt essential oil, mandarin essential oil, marjoram essential oil, mate 1 essential oil, Melissa essential oil, menthol essential oil, menthyl acetate essential oil, molasses essential oil, mustard essential oil, naringin essential oil, neroli essential oil, nutmeg essential oil, onion essential oil, orange essential oil, *origanum* essential oil, palmarosa essential oil, paprika essential oil, parsley essential oil, pepper essential oil, peppermint essential oil, peruvian balsam essential oil, petitgrain essential oil, pimento essential oil, pipsissewa leaves essential oil, pomegranate essential oil, prickly ash bark essential oil, rose essential oil, rosemary essential oil, rue essential oil, saffron essential oil, sage essential oil, St. John's bread essential oil, savory essential oil, *schinus molle* essential oil, sloe berries essential oil, spearmint essential oil, spike lavender essential oil, tamarind essential oil, tangerine essential oil, tannic acid essential oil, tarragon essential oil, tea essential oil, *triticum* essential oil, vanilla essential oil, violet essential oil, wild cherry bark essential oil, ylang-ylang essential oil, zedoary bark essential oil.

In some embodiments, the one or more essential oils include one or more of cinnamon essential oil, thyme essential oil, oregano essential oil, *Cassia* redistilled Chinese oil; thyme oil red: origanium: origanium oil organic: thyme white oil: mustard oil: organic oregano; cinnamon bark oil: thyme oil white: allspice leaf oil: thyme oil red organic: cinnamon bark oil organic: clove bud redistilled oil: clove leaf redistilled oil: anise star oil: basil Indian oil; caraway oil: spearmint far west native: rosemary Spanish: lemongrass Indian oil: peppermint Chinese type: palmarosa Indian oil: lavadin grosso maerican: rosemary Moroccan: marjoram sweet oil: rosemary Spanish: rosemary organic: rosemary verbenone organic: lavender spike pure oil: juniperberry oil: petitgrain: *eucalyptus* glob organic oil: coriander seed oil: balsam peru oil: citronella java oil: garlic Chinese oil: bergamot BF oil: ginger chinese oil: chamomile roman oil: tangerine: melissa oil: pepper black Indian oil: lime expressed Mexican oil: lemon argentina oil: cardamom oil: carrot seed oil: nutmeg oil: fennel sweet oil: organic turmeric essential oil: grapefruit pink oil: grapefruit white oil: grapefruit red oil: mandarin green Italian oil: mandarin red oil: turmeric essential oil; and oleoresin *capsicum*.

As mentioned above, in some embodiments, the essential oils can be derived from plants (i.e., "natural" essential oils) and additionally or alternatively their synthetic analogues. Some embodiments comprise a combination of natural and synthetic essential oils. In some embodiments, synthetic essential oils can be a "nature's equivalent" synthetic blend, which generally mimics an essential oil assay of a natural essential oil by including at least 2, at least 5, at least 10, at least 15, at least 20, or any increment thereof, of the most critical essential oils within a natural essential oil. A critical essential oil can be determined by weight percent, and/or by pharmacological efficacy. For example, in one embodiment, a nature's equivalent synthetic oil can comprise the following constitutions as provided in Table 1:

TABLE 1

Nature's Equivalent Synthetic Thyme Essential Oil:

| Constituent | Wt. % |
| --- | --- |
| Thymol | 42.7-44.08 |
| para-Cymene | 26.88-27.09 |
| Linalool | 4.3-4.34 |
| alpha-Pinene | 4.1-4.26 |
| alpha-Terpineol | 3.14-3.14 |
| 1,8-Cineole | 2.82-3.01 |
| beta-Caryophellene | 1.98-2.27 |
| Limonene | 1.59-1.78 |
| delta-3-Carene | 1.3-1.41 |
| beta-Myrcene | 1.26-1.31 |
| Linalyl Acetate | 1.11-1.24 |
| beta-Pinene | 1.04-1.22 |
| Terpinen-4-ol | 0.96-1.14 |
| alpha-Caryophyllene | 0.71-0.71 |
| gamma-Terpinene | 0.7-0.7 |
| Sabinene | 0.37-0.5 |
| Borneol | 0.27-0.32 |
| Camphene | 0.13-0.17 |

The disclosure herein indicates the efficacy of compositions comprising a plurality of essential oils which provide a synergistic effect beyond essential oils utilized in isolation. Further, the essential oils do not exhibit any antagonistic effects between essential oil moieties within an essential oil composition or feed composition. An essential oil composition can include an essential oil fraction and one or more additional components. The ratio of the essential oil fraction to the one or more additional components in an essential oil composition can depend on several factors such as administration method, and the nutritional/health needs and/or palate of a consuming subject, among others. In some embodiments, a consuming subject comprises animals. In some embodiments, a consuming subject comprises humans. Compositions can comprise additional components including carriers, emulsifiers, and stabilizers, among others. Compositions as provided herein can be in the form of an emulsion. For example, in some embodiments, the feed compositions comprise an essential oil composition, wherein the essential oil composition comprises one or more essential oils and at least one emulsifier, wherein the one or more essential oils are present as an emulsion.

Essential oils suitable for inclusion in the essential oil compositions include any of those disclosed herein. For example, in some embodiments, the essential oil compositions include, without limitation, one or more of cinnamon essential oil, thyme essential oil, oregano essential oil, capsicum essential oil, Cassia redistilled Chinese oil; thyme oil red: origanium; origanium oil organic: thyme white oil: mustard oil: organic oregano; cinnamon bark oil: thyme oil white: allspice leaf oil: thyme oil red organic: cinnamon bark oil organic: clove bud redistilled oil: clove leaf redistilled oil: anise star oil: basil Indian oil: caraway oil: spearmint far west native: rosemary Spanish: lemongrass Indian oil: peppermint Chinese type: palmarosa Indian oil: lavadin grosso maerican: rosemary Moroccan: marjoram sweet oil: rosemary Spanish: rosemary organic: rosemary verbenone organic: lavender spike pure oil: juniperberry oil: petitgrain: eucalyptus glob organic oil: coriander seed oil: balsam peru oil: citronella java oil: garlic Chinese oil: bergamot BF oil: ginger chinese oil: chamomile roman oil: tangerine; melissa oil: pepper black Indian oil: lime expressed Mexican oil: lemon argentina oil; cardamom oil: carrot seed oil: nutmeg oil: fennel sweet oil: organic turmeric essential oil; grapefruit pink oil: grapefruit white oil: grapefruit red oil: mandarin green Italian oil; mandarin red oil: turmeric essential oil: oleoresin capsicum.

In some embodiments, the essential oils include oils from the classes of terpenes, terpenoids, phenylpropenes, or combinations thereof. In some embodiments, the essential oils include oils of plants from the Labiatae or Lamiaceae family, and the Lauraceae family, including hybrids of plants from one or both families. Suitable essential oils from the Lauraceae family can comprise those from the Cinnamomum genus. Within the Cinnamomum genus, suitable species can include Cinnamomum burmannii, Cinnamomum cassia, Cinnamomum camphora, Cinnamomum loureiroi, Cinnamomum mercadoi, Cinnamomum oliveri, Cinnamomum osmophloeum, Cinnamomum ovalifolium, Cinnamomum parthenoxylon, Cinnamomum pedunculatum, Cinnamomum subavenium, Cinnamomum tamala, Cinnamomum verum, Cinnamomum verum, and hybrids thereof.

Suitable essential oils from the Lamiaceae family can comprise those from one or more of the Thymus genus, the Origanum genus, the Monarda genus. Within the Thymus genus, a non-limiting list of suitable species can include Thymus caespititius, Thymus capitatus, Thymus carnosus, Thymus citriodorus, Thymus glandulosus, Thymus Herbaborana, Thymus hyemalis, Thymus integer, Thymus pseudolanuginosus (formerly T. lanuginosus), Thymus mastichinia, Thymus montanus, Thymus moroderi, Thymus pannonicus, Thymus praecox, Thymus pulegioides, Thymus serpyllum, Thymus vulgaris, Thymus zygis, and hybrids thereof. Within the Origanum genus, a non-limiting list of suitable species can include Origanum amanum, Origanum compactum, cordifolium, Origanum dictamnus, Origanum laevigatum, Origanum libanoticum, Origanum majorana, Origanum microphyllum, Origanum onites, Origanum rotundifolium, Origanum scabrum, Origanum syriacum, Origanum vulgare, and hybrids thereof. Within the Monarda genus, a non-limiting list of suitable species can include Monarda citriodora, Monarda clinopodioides, Monarda didyma, Monarda fistulosa, Monarda media, Monarda punctata, and hybrids thereof.

Additional examples of essential oils include, without limitation, one or more of the following essential oils: cassia redistilled Chinese oil, thyme oil red, Origanium, natural oregano, origanum oil (organic), thyme white food grade, mustard oil, rosemary essential oil, organic oregano, cinnamon bark oil, thyme oil white, allspice leaf oil, thyme oil red organic, cinnamon bark oil organic, clove bud redistilled oil, clove leaf redistilled oil, anise star oil, basil Indian oil, caraway oil, spearmint far west native, rosemary Spanish oil, lemongrass Indian oil, peppermint Chinese type, palmarosa Indian oil, lavadin grosso American oil, rosemary Moroccan oil, marjoram sweet oil, rosemary organic oil, rosemary verbenone organic oil, lavender spike pure oil, juniperberry oil, petitgrain oil, eucalyptus glob organic oil, coriander seed oil, balsam Peru oil, citronella java oil, garlic Chinese oil, bergamot BF oil, Ginger Chinese Oil, Chamomile Roman Oil, Tangerine oil, Melissa oil, pepper black Indian oil, lime expressed mexican oil, lemon argentina oil, cardamom $CO_2$ oil, carrot seed oil, nutmeg oil, fennel sweet oil, organic turmeric essential oil, grapefruit pink oil, grapefruit whit eoil, grapefruit red oil, mandarin green Italian oil, mandarin red oil, oleoresin capsicum (106) oil, and the like.

In some embodiments, the essential oils can further include lavender essential oils from the Lavandula genus, Mexican bay leaf essential oils from the Liteas genus (e.g., L. glaucescens), West Indian bay tree essential oils from the Pimenta genus (e.g., P. racemosa), Indonesian bay leaf essential oils from the Syzygium genus, bay laurel essential oils from the *Laurus* genus (e.g., *L. nobilis*), California bay laurel essential oils from the *Umbellularia* genus (e.g., *U. californica*), lemon grass essential oils from the Cymbopogon genus (e.g., *C. ambiguous, C. citratus, C. flexuosus, C. martini, C. nardus, C. schoenanthus*), spearmint and peppermint essential oils from the Mentha genus (e.g., *M. spicata, M. piperita*), rosemary essential oils from the *Rosmarinus* genus (e.g., *R. officinalis*), sage essential oils from the *Salvia* genus (e.g., *S. sclarea*), hybrids thereof, or combinations thereof.

In some embodiments, an essential oil composition can include an essential oil fraction comprising three essential oils from the Lauraceae family and/or the Lamiaceae family. In some embodiments, an essential oil composition can include an essential oil fraction comprising cinnamon essential oil from the *Cinnamomum* genus, thyme essential oil from the *Thymus* genus, and oregano essential oil the *Origanum* genus. In some embodiments, an essential oil composition can include an essential oil fraction comprising synthetic cinnamaldehyde and thyme essential oils from the *Thymus* genus and oregano essential oil from the *Origanum* genus. In some embodiments, oregano essential oil can comprise carvacrol. Additionally or alternatively, thyme essential oil can comprise thymol.

In some embodiments, the essential oil fraction can comprise about 1% to about 49.5% oregano essential oil, about 1% to about 49.5% thyme essential oil, and about 1% to about 49.5% cinnamon essential oil. In other embodiments, the essential oil fraction can comprise about 5% to about 47.5% oregano essential oil, about 5% to about 47.5% thyme essential oil, and about 5% to about 47.5% cinnamon essential oil. In other embodiments, the essential oil fraction can comprise about 10% to about 45% oregano essential oil, about 10% to about 45% thyme essential oil, and about 10% to about 45% cinnamon essential oil. In other embodiments, the essential oil fraction can comprise about 15% to about 42.5% oregano essential oil, about 15% to about 42.5% thyme essential oil, and about 15% to about 42.5% cinnamon essential oil. In other embodiments, the essential oil fraction can comprise about 20% to about 40% oregano essential oil, about 20% to about 40% thyme essential oil, and about 20% to about 40% cinnamon essential oil. In other embodiments, the essential oil fraction can comprise about 25% to about 37.5% oregano essential oil, about 25% to about 37.5% thyme essential oil, and about 25% to about 37.5% cinnamon essential oil. In other embodiments, the essential oil fraction can comprise about 30% to about 35% oregano essential oil, about 30% to about 35% thyme essential oil, and about 30% to about 35% cinnamon essential oil. In other embodiments, the essential oil fraction can comprise about 33.33% oregano essential oil, about 33.33% thyme essential oil, and about 33.33% cinnamon essential oil.

Many essential oil compositions comprise an essential oil fraction comprising an effective amount of carvacrol, an effective amount of thymol, and an effective amount of cinnamaldehyde. In an essential oil composition including an essential oil fraction comprising oregano essential oil, thyme essential oil, and cinnamon essential oil, the essential oil fraction can comprise three or more natural essential oils wherein the combined essential oils comprise at least an effective amount of carvacrol, at least an effective amount of thymol, and at least an effective amount of cinnamaldehyde. Suitable essential oils can include essential oils from the *Cinnamomum* genus, essential oils from the *Origanum* genus, essential oils from the *Thymus* genus, essential oils from the *Monarda* genus (e.g., *M. citriodora, M. clinopodioides, M. didyma, M. fistulosa, M. media, M. punctata*), essential oils from the *Trachyspermum* genus (e.g., *T. ammi*), essential oils from the Nigella genus (e.g., *N. sativa*), and combinations thereof. Other essential oils can be used such that effective amounts of carvacrol, thymol, and cinnamaldehyde are achieved in the essential oil fraction.

In an essential oil composition including an essential oil fraction comprising oregano essential oil, thyme essential oil, and synthetic cinnamaldehyde, the essential oil fraction can comprise two or more natural essential oils and synthetic cinnamaldehyde, wherein the combined essential oils and synthetic cinnamaldehyde comprise at an effective amount of carvacrol, at least an effective amount of thymol, and at least an effective amount of cinnamaldehyde. Suitable essential oils can include essential oils from the *Cinnamomum* genus, essential oils from the *Origanum* genus, essential oils from the *Thymus* genus, essential oils from the *Monarda* genus (e.g., *M. didyma*, and *M. fistulosa*), essential oils from the *Trachyspermum* genus (e.g., *T. ammi*), essential oils from the Nigella genus (e.g., *N. sativa*), and combinations thereof. Still other natural essential oils can be used such that effective amounts of carvacrol, thymol, and cinnamaldehyde are achieved in the essential oil fraction.

In some embodiments, the feed compositions can comprise about 0% to about 100% by weight essential oil(s) or essential oil compound(s). In some embodiments, the weight percent of the essential oil composition, by total weight of the feed composition, is about or up to about 0.1 wt. %, up to about 0.5 wt. %, up to about 1.0 wt. %, up to about 2 wt. %, up to about 3 wt. %, up to about 4 wt. %, up to about 5 wt. %, up to about 6 wt. %, up to about 7 wt. %, up to about 8 wt. %, up to about 9 wt. %, up to about 10 wt. %, up to about 11 wt. %, up to about 12 wt. %, up to about 15 wt. %, up to about 20 wt. %, up to about 22 wt. %, up to about 24 wt. %, up to about 26 wt. %, up to about 28 wt. %, up to about 30 wt. %, up to about 32 wt. %, up to about 34 wt. %, up to about 36 wt. %, up to about 38 wt. %, up to about 40 wt. %, up to about 42 wt. %, up to about 44 wt. %, up to about 46 wt. %, up to about 48 wt. %, up to about 50 wt. %, or any increment or value thereof, or at least one of the aforementioned weight percentages, or no more than the aforementioned weight percentages.

In some embodiments in which the feed additive composition comprises a cobalt compound, a yeast component, and an essential oil composition, the amount of the essential oil composition is between about 0.5 and about 15 percent (by weight) based on a total weight of the feed additive composition, between about 7 and about 14 percent, between about 3.5 and about 12 percent, and between about 3.5 and about 7.5 percent.

In some embodiments, the ratio of yeast to the essential oil composition is between about 140:1 and about 6:1, between about 75:1 and about 9:1, between about 30:1 and 10:1, and between about 28:1 and 18:1.

Some essential oil compositions comprise an essential oil fraction comprising an effective amount of carvacrol, an effective amount of thymol, and an effective amount of cinnamaldehyde. An effective amount of carvacrol can comprise at least about 10 wt. %, at least about 15 wt. %, at least about 20 wt. %, at least about 25 wt. %, at least about 30 wt. %, or at least about 33 wt. % of the essential oil fraction. An effective amount of thymol can comprise at least about 10 wt. %, at least about 15 wt. %, at least about 20 wt. %, at least about 25 wt. %, at least about 30 wt. %, or at least about 33 wt. % of the essential oil fraction. An effective amount of cinnamaldehyde can comprise at least about 10 wt. %, at least about 15 wt. %, at least about 20 wt. %, at least about 25 wt. %, at least about 30 wt. %, or at least about 33 wt. % of the essential oil fraction. In some embodiments, oregano essential oil can be replaced by one or more oils which include at least 45 wt. % carvacrol, at least 55 wt. % carvacrol, at least 65 wt. % carvacrol, or at least 75 wt. % carvacrol. In some embodiments, thyme essential oil can be replaced by one or more oils which include at least 30 wt. % thymol, at least 35 wt. % thymol, at least 40 wt. % thymol, or at least 45 wt. % thymol. In some embodiments, cinnamon essential oil can be replaced by one or more oils which include at least 35 wt. % cinnamaldehyde, at least 40 wt. % cinnamaldehyde, at least 50 wt. % cinnamaldehyde, or at least 75 wt. % cinnamaldehyde. Suitable sources of effective amounts of carvacrol, thymol, and/or cinnamaldehyde can include natural essential oils and/or synthetic essential oils.

Essential oil compositions can further comprise one or more of an effective amount of paracymene, an effective amount of eugenol, or an effective amount of citronella. An effective amount of paracymene can comprise at least about 5 wt. %, at least about 7.5 wt. %, at least about 10 wt. %, or at least about 12.5 wt. % of the essential oil fraction. An effective amount of eugenol can comprise at least about 5 wt. %, at least about 7.5 wt. %, at least about 10 wt. %, or at least about 12.5 wt. % of the essential oil fraction. An effective amount of citronella can comprise at least about 5 wt. %, at least about 7.5 wt. %, at least about 10 wt. %, or at least about 12.5 wt. % of the essential oil fraction.

In some embodiments, the essential oil fraction comprises 100% of the essential oil composition. An essential oil composition can further comprise a carrier. Carriers are ideally inert materials which do not react with the active components (i.e., the essential oil fraction) of the composition chemically, or bind the active components physically by adsorption or absorption. Liquid carriers include water, pure water, such as reverse osmosis water, milk, milk replacers, natural and/or commercial liquid feeds, or other liquids germane to animal dietary needs. Milk replacers can be formulated to generally mimic the content of milk. For example, a milk replacer can have a composition similar to that shown in Table 2:

TABLE 2

Example Milk Replacer Formula

| | |
|---|---|
| Crude Protein, minimum | 22.50% |
| Lysine, minimum | 1.60% |
| Crude Fat, minimum | 16.50% |
| Crude Fiber, maximum | 0.50% |
| Calcium, minimum | 0.65% |
| Calcium, maximum | 1.15% |
| Phosphorus, minimum | 0.60% |
| Sodium, minimum | 0.50% |
| Sodium, maximum | 1.00% |
| Selenium, minimum | 0.25 ppm |
| Zinc, minimum | 50 ppm |

The composition can be at least about 50% liquid carrier by weight, at least about 75% liquid carrier by weight, at least about 85% liquid carrier by weight, or at least about 90% liquid carrier. In some embodiments, the composition will be about 80% to about 99% liquid carrier, about 85% to about 98% liquid carrier, about 90% to about 95% liquid carrier, or about 91% to about 94% liquid carrier. In other embodiments, the composition can be about 60% liquid carrier to about 74% liquid carrier, about 63% liquid carrier to about 71% liquid carrier, about 66% liquid carrier to about 68% liquid carrier, or about 67% liquid carrier.

Solid carriers can include limestone, diatomaceous earth, and animal feed. Carriers such as limestone, diatomaceous earth, and the like, are useful pre-feed carriers in that they may be first combined with an essential oil fraction to facilitate transportation and/or subsequent combination of the essential oil composition with a dry carrier such as animal feed. Animal feed can include hay, straw, corn husks, wheat, oats, barley, seeds, commercial livestock feed, and the like. In some embodiments where an essential oil composition comprises an essential oil fraction and a pre-feed carrier, the ratio of pre-feed carrier to the essential oil fraction can be at least 10:1, at least 15:1, at least 17:1, at least 18:1, or at least 20:1. In some embodiments, where an essential oil composition comprises an essential oil fraction and a carrier, with or without a pre-feed carrier, the ratio of carrier to the essential oil fraction can be at least about 1,000:1, at least about 4,500:1, at least about 9,000:1, at least about 20,000:1, at least about 35,000:1, or at least about 50,000:1.

The total amount of carrier in a composition can be determined based on the dietary needs of an animal, the tolerance of an animal to essential oil fraction, and other factors. Tolerance can include one or more of an animal's palatability and gastrointestinal tolerance to an essential oil fraction.

An essential oil composition can further comprise one or more dedusting agents. Dedusting agents can comprise vegetable oil, olive oil, mineral oil and the like. The amount of dedusting agent in an essential oil composition can be determined based on the amount required to keep dust low while also allowing a dry composition to be "free flowing". A suitable "free flowing" characteristic can be determined by a funnel flow test or free flow test. A dedusting agent can be included in a feed in an amount between about 5-40 lbs/ton.

In some embodiments, a dedusting agent can be used as part of an essential oil composition. In some embodiments, a dedusting agent can be used independently of an essential oil composition. A feed additive composition comprising a yeast component and a cobalt compound can further comprise a mineral oil or other dedusting compound. In an example, the mineral oil can be about one percent (1%) by weight based on a total weight of the feed additive composition.

As mentioned above, the essential oil composition may be provided in the form of an emulsion. Accordingly, in some embodiments, the essential oil composition include one or more emulsifiers. In some embodiments, one or more emulsifiers are added to an essential oil composition. An emulsified essential oil fraction can increase the efficacy of an essential oil composition when ingested by a subject, and can make essential oil compositions more palatable to animals which consume the compositions orally. An essential oil fraction can be combined with an emulsifier and a dry carrier, or alternatively an essential oil fraction can be combined with an emulsifier and a liquid carrier, as disclosed above, to form an emulsion. The emulsifier can be combined with an essential oil fraction in a ratio of about 3:1 to about 1:3, about 2:1 to about 1:2, about 1.5:1 to about 1:1.5, or about 1:1. An essential oil composition comprising an essential oil fraction, a liquid carrier, and an emulsifier can have an average essential oil droplet size of less than about 25 microns, less than about 15 microns, less than about 10 microns, less than about 7.5 microns, or less than about 5 microns. In some embodiments, the average droplet size is less than about 7 microns, less than about 6 microns, less than about 5 microns, less than about 4 microns, or less than about 3 microns. As used herein, "droplet size" refers to the average size of an essential oil droplet within an emulsion.

The feed composition and/or essential oil composition can comprise anywhere between about 0% to about 100% by weight emulsifier(s). An emulsifier combined with a liquid carrier can generally be referred to as a liquid emulsifier. In some embodiments, an emulsion can comprise up to about 35%, up to about 40%, up to about 45%, or up to about 50% essential oil fraction and emulsifier, with the balance comprising a liquid carrier. In some embodiments, an emulsion can comprise less than about 20%, less than about 15%, less than about 10%, about 5%, or less than about 5% essential oil fraction and emulsifier, with the balance comprising a liquid carrier. In some embodiments, an emulsion can comprise about 40% to about 60%, or about 45% to about 55% essential oil fraction and emulsifier, with the balance comprising a liquid carrier. In some embodiments, an emulsion can comprise about 1% to about 10%, about 2.5% to about 7.5%, or about 5% essential oil fraction and emulsifier, with the balance comprising a liquid carrier. In many embodiments the liquid carrier is water. The liquid carrier content can vary depending on the amount and type of emulsifier.

One or more emulsifiers can be used to form an emulsion. In some embodiments, one or more emulsifiers can additionally or alternatively be used as a stabilizer. Stabilizers can be used to alter the viscosity of an emulsion. Altering a viscosity can include maintaining a viscosity, increasing a viscosity, or decreasing a viscosity. A suitable emulsifier can be an emulsifier capable of achieving a threshold droplet size. In some embodiments a suitable emulsifier can achieve a suitable emulsion droplet size of less than about 25 microns, less than about 15 microns, less than about 10 microns, less than about 7.5 microns, or less than about 5 microns. In other embodiments, a suitable emulsifier can achieve a suitable emulsion droplet size of less than about 7 microns, less than about 6 microns, less than about 5 microns, less than about 4 microns, or less than about 3 microns. In other embodiments, the emulsion droplet size is in the range of 0.01 microns to about 100 microns, or any increment thereof. An emulsion having a droplet size below a suitable threshold enhances the efficacy of an essential oil composition.

A suitable emulsifier is larch arabinogalactan. Arabinogalactan generally comprises arabinose and galactose monosaccharides, and can be synthetic or natural. Natural arabinogalactan can be derived from plants or microbes. For example, arabinogalactan can be derived from larch trees, and many fruits, vegetables, and beans. In some embodiments, arabinogalactan is a preferred emulsifier because it is capable of achieving a desired droplet size and also acts as an antioxidant against many ROS, including peroxyl radicals, hydroxyl radicals, peroxynitrite, superoxide anions, and singlet oxygen. Accordingly, the hydrophilic characteristics of arabinogalactan enhance the cellular coverage of an essential oil composition. A particular type of arabinogalactan is larch arabinogalactan.

In some embodiments, the dietary fiber includes larch arabinogalactan. The larch arabinogalactan can generally include any composition comprising arabinogalactan and optionally other species, such as polyphenols. The larch arabinogalactan can be extracted or derived from any species in the genus *Larix*. For example, species of the genus *Larix* include, but are not limited to, *Larix laricina, Larix lyallii, Larix leptolepis, Larix occidentalis, Larix decidua, Larix dahurica, Larix sibirica, Larix gmelinii, Larix kaempferi, Larix czekanowskii, Larix potaninii, Larix mastersiana, Larix griffithii*, and hybrids thereof. The larch arabinogalactan is available from commercial sources. It can be provided in solid form, such as in the form of a powder, or it can be provided in liquid form.

The arabinogalactan can be characterized as a water-soluble, highly or densely branched polysaccharide. The arabinogalactan can generally include any compound composed of galactose units and arabinose units in an approximate ratio of about 100:1 to about 1:1. For example, the arabinogalactan can have a galactan backbone with side chains containing galactose units and arabinose units, wherein a ratio of the galactose units to arabinose units is about 6:1 or about 7.5:1. In an embodiment, the arabinogalactan can be characterized as having a backbone of (1→3)-linked β-D-galactopyranosyl units, each of which can bear a substituent at the C6 position. Most of these side chains can be galactobiosyl units containing a (1→6)-β-D-linkage and α-L-arabinofuranosyl units. These shall not be limiting, as the arabinogalactan can also include arabinogalactan derivatives, such as lipidated and/or quaternized forms of arabinogalactan.

The arabinogalactan can vary in molecular weight from low molecular weight polymers to large macromolecules. The molecular weight of the arabinogalactan can range from about 1,000 Daltons to about 2,500,000 Daltons, or any increment thereof. For example, the molecular weight of the arabinogalactan can range from about 6,000 Daltons to about 2,500,000 Daltons, about 6,000 Daltons to about 300,000 Daltons, about 3,000 Dalton to about 120,000 Dalton, about 15,000 Dalton to about 60,000 Dalton, or about 40,000 Dalton to about 60,000 Dalton, among other ranges.

The larch arabinogalactan can include other species. For example, typically, the larch arabinogalactan comprises polyphenols. The polyphenols can include any compound having two or more phenol groups or moieties. Examples of polyphenols include, but are not limited to, one or more of flavonoids, aromadendrines, anthocyanins, catecholins, catechins, and taxifolins. In an embodiment, the polyphenols include at least flavonoids, such as quercetin. The larch arabinogalactan typically comprises about 1 wt % to about 4 wt % of polyphenols; however, higher and lower concentrations are possible and within the scope of the present disclosure.

Other suitable emulsifiers include polydextrose, chitin, *psyllium*, methyl-cellulose, hydrolyzed guar, guar, soy polysaccharide, oat bran, pectin, inulin, Fructooligosaccharides (FOS), xanthan gum, alginate, chemically modified cellulosic, Acacia, and gum Arabic.

In some embodiments, a suitable emulsifier can include a tannin compound, such as tannic acid. Tannin can be used as an alternative to or in combination with the emulsifiers described above. In some embodiments, a liquid emulsifier can comprise about 100% tannic acid, about 80% to about 95% tannic acid, about 60% to about 85% tannic acid, about 40% to about 60% or about 1% to about 50% tannic acid, with the balance being a liquid carrier.

The improvements in performance may include, for example and without limitation, one or more of the following: increasing milk production in dairy cows, stimulating native rumen microbes to increase enzyme production (e.g., for fiber digestion), while also selectively targeting the growth of beneficial microbes, including microbes involved in the production of enzymes: increasing the production and/or rate of production of at least one volatile fatty acid in the rumen: decreasing the production and/or rate of production of methane; increasing the digestion and/or rate of digestion by the ruminant; and decreasing a concentration of ammonia in the rumen. In some embodiments, the feed additive compositions impact the microbial community, impact some some fungi in rumen, impact protein metabolism, impact activation enzymes with enzyme activation, act as a growth enhancer for the bacteria, enhance fiber digestion, stabilizing ruminal function, stabilizing ruminal pH, improving rumen health, stimulating digestive microflora which positively affects dry matter intake, rumen pH, and nutrient digestibility: complements and stimulates the growth of ruminal cellulolytic or fiber-digesting bacteria, increasing rate and efficiency of ruminal fermentation, among other things.

FIG. 1 is a flowchart of a method of improving performance of a ruminant, according to one or more embodiments of the invention. As shown in FIG. 1, the method may include administering 106 to a ruminant 104 an amount of a feed additive composition 102 sufficient to increase production of at least one enzyme in a rumen, increase production of at least one volatile fatty acid in the rumen, and/or decrease production of methane in the rumen, wherein the feed additive composition 102 includes at least one of the following: a chelated cobalt compound, a yeast component, and an essential oil composition (as described herein).

The administering 106 is not particularly limited and can include any method suitable for delivering the composition to the subject. The composition can be administered to the subject in solid (e.g., pellets, powder, etc.) or liquid form. For example, the composition can be administered as nutritional or feed supplements. In an embodiment, the administering includes mixing the composition with water and/or feed. In an embodiment, the administering includes administering by gavage. In an embodiment, the administering includes bolus feeding. Administering 106 may include combining the feed additive composition 102 with animal feed. Administering 106 may include oral ingestion of the feed additive composition 102 as a feed or liquid, ingesting the feed additive composition in an encapsulated form, or applying the feed additive composition 102 topically. Pill-based or encapsulated administrations 106 can be ideal for compositions 102 which are not sufficiently palatable or an animal. However, administration 106 via water or food-based carriers can be preferred for ease of administration 106. Administering 106 may include providing the product as a feed or feed supplement. Administering 106 may include providing the product to the ruminant through ingestion of a plant containing the product. Administering 106 may include administering by gavage, bolus feeding, oral ingestion as a feed or liquid, ingesting in an encapsulated form, or topical application. These are provided as examples and thus shall not be limiting. Other methods of administering known in the art can be used herein without departing from the scope of the present disclosure.

The amount of the feed additive composition 102 administered 106 to the ruminant 104 can depend on the species of the ruminant, the size of the ruminant, and the health status of the ruminant. For example, the feed additive compositions can be administered regularly (i.e., daily) as a routine nutritional and health supplement, as an intervention (i.e., for several days or for the duration of a particular episode) in response to or in conjunction with increased stress, disease, birth, or other factors, or as a one-time administration during birth or a severe infection, disease, or injury. In some embodiments, the feed additive composition is administered to the ruminant at a rate of about 2 kg per head per day to about 12 kg per head per day.

Figure 2:
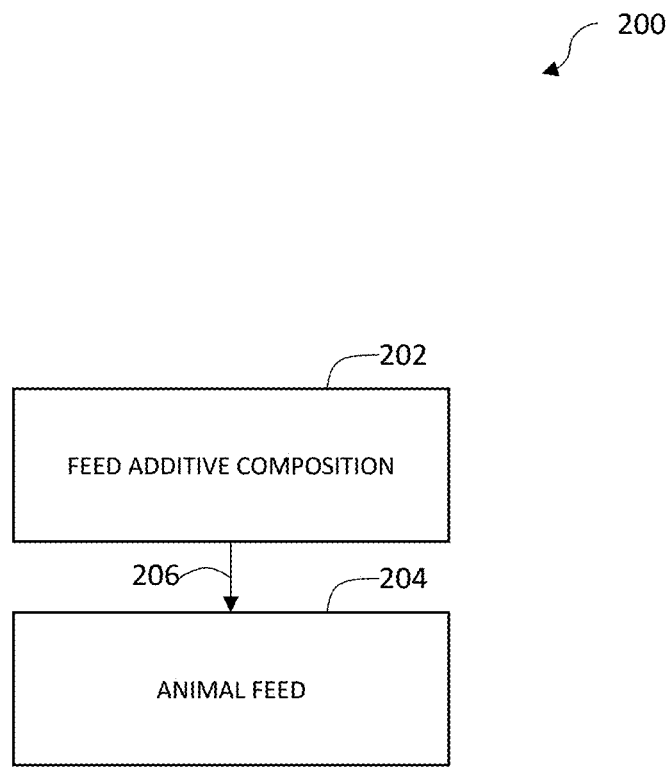
FIG. 2 is a flowchart of a method of preparing a feed additive composition for improving performance of a ruminant, according to one or more embodiments of the present disclosure.

FIG. 2 is a flowchart of a method of preparing a feed additive composition for improving performance of a ruminant, according to one or more embodiments of the present disclosure. As shown in FIG. 2, the method of preparing the feed additive composition may include applying 206 a feed additive composition 202 to animal feed 204, wherein the feed additive composition 202 includes at least one of the following: a chelated cobalt compound, a yeast component, and an essential oil composition (as described herein).

Example 1

Stimulating Rumen Microbes

Figure 3:
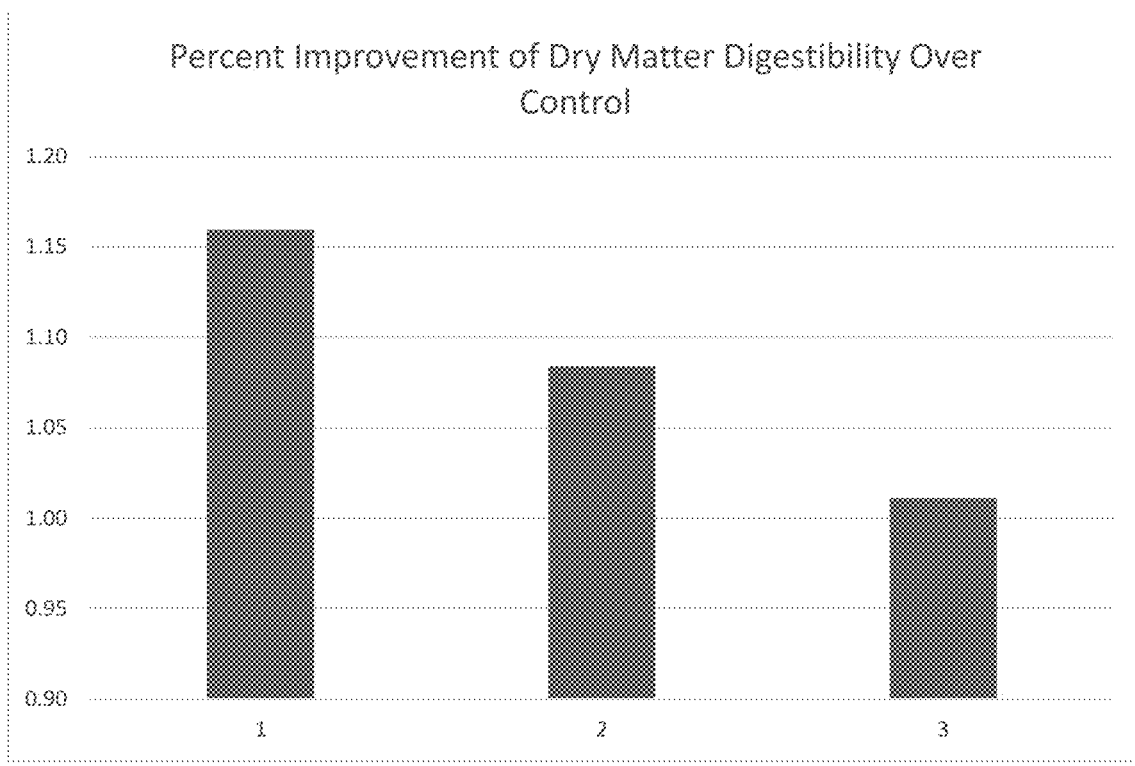
FIG. 3 is a graphical view of percent improvement of dry matter digestibility over control, according to one or more embodiments of the invention.
Figure 4:
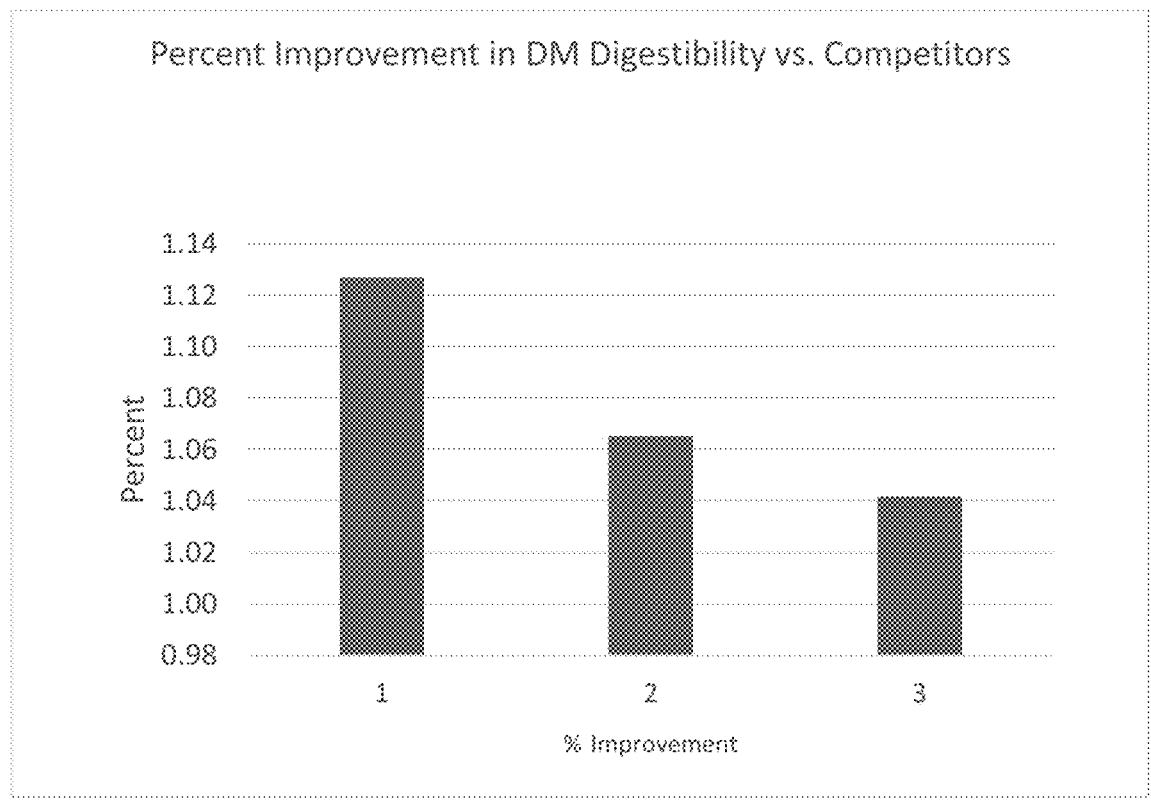
FIG. 4 is a graphical view of percent improvement of dry matter digestibility over competitor A and competitor D, according to one or more embodiments of the invention.

A formulation of a feed additive composition was prepared to evaluate the formulation's ability to stimulate rumen microbes. The formulation included about 96.70% by weight of a yeast culture, about 2.30% by weight of a cobalt lactate compound, and about 1.00% by weight of a mineral oil. The formulation was administered to ruminants. While not wishing to be bound to a theory, it is believed that the feed additive composition stimulated native rumen microbes to release enzymes that increased fiber digestibility and released more energy from feed. By combining the effects of the cobalt lactate and the yeast component, the feed additive composition unexpectedly increased fiber digestibility to a greater extent than the summation of the individual contributions from the cobalt lactate and the yeast component. This is presented in FIGS. 3-4 which provide graphical views of percent improvement of dry matter digestibility over control, according to one or more embodiments of the invention.

Figure 5A:
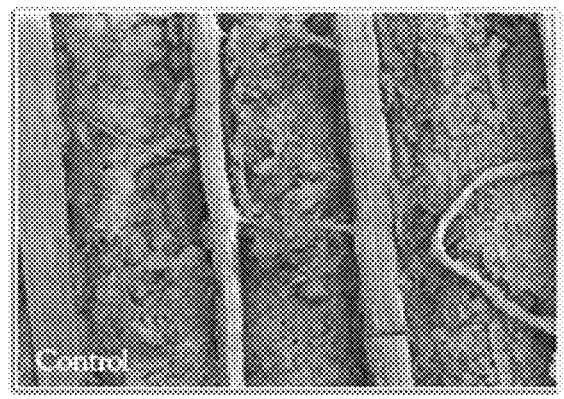
FIGS. 5A-5B are SEM images illustrating the additional release of energy through cell degradation of a silage leaf for (A) a control and (B) a feed additive composition, according to one or more embodiments of the invention.
Figure 5B:
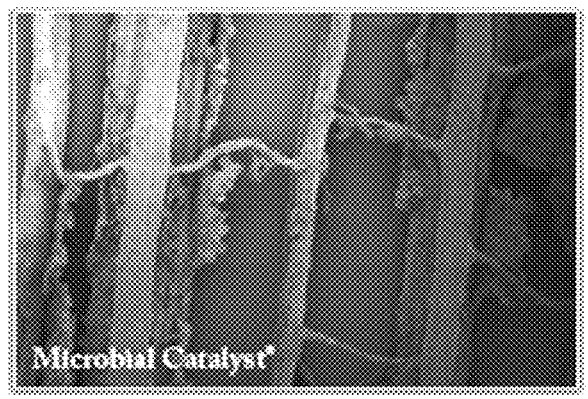

In multiple trials with high-forage diets, fiber digestibility was improved 12-24% over the control. As shown in FIGS. 5A-5B, greater cell wall degradation of a silage leaf, and by that greater release of energy, was observed in ruminants fed the feed additive composition over the control. The yeast component further increased rumen microbial growth by feeding the microbes. Fermented yeast metabolites, amino acids, enzymes, and minerals provided the food and fuel rumen microbes required to grow more efficiently, with additional yeast components passing through the rumen to support gut microflora and immunity.

Example 2

Ammonia Reduction

Formulations 0 to 9 were prepared to evaluate and compare the various formulations effect on gas production. The formulations are summarized in Table 1 below:

TABLE 1

Treatment designations for the in vitro study.

| Treatment Description | Treatment Number |
| --- | --- |
| Control, feed, buffer, rumen fluid | 0 |
| Arabinogalactan Liquid | 1 |
| Cobalt Lactate Feed | 2 |
| Yeast Culture (Emprove MX, Emmert) | 3 |
| Emulsified Essential Oils (CTO) dry | 4 |
| Non-emulsified Essential Oils (CTO) pure off | 5 |
| Cobalt lactate + Yeast Culture | 6 |
| Cobalt lactate + Emulsified Essential Oils (CTO) dry | 7 |
| Yeast Culture + Emulsified Essential Oils (CTO) dry | 8 |
| Cobalt lactate + Yeast Culture + Emulsified Essential Oils (CTO) dry | 9 |

Figure 6:
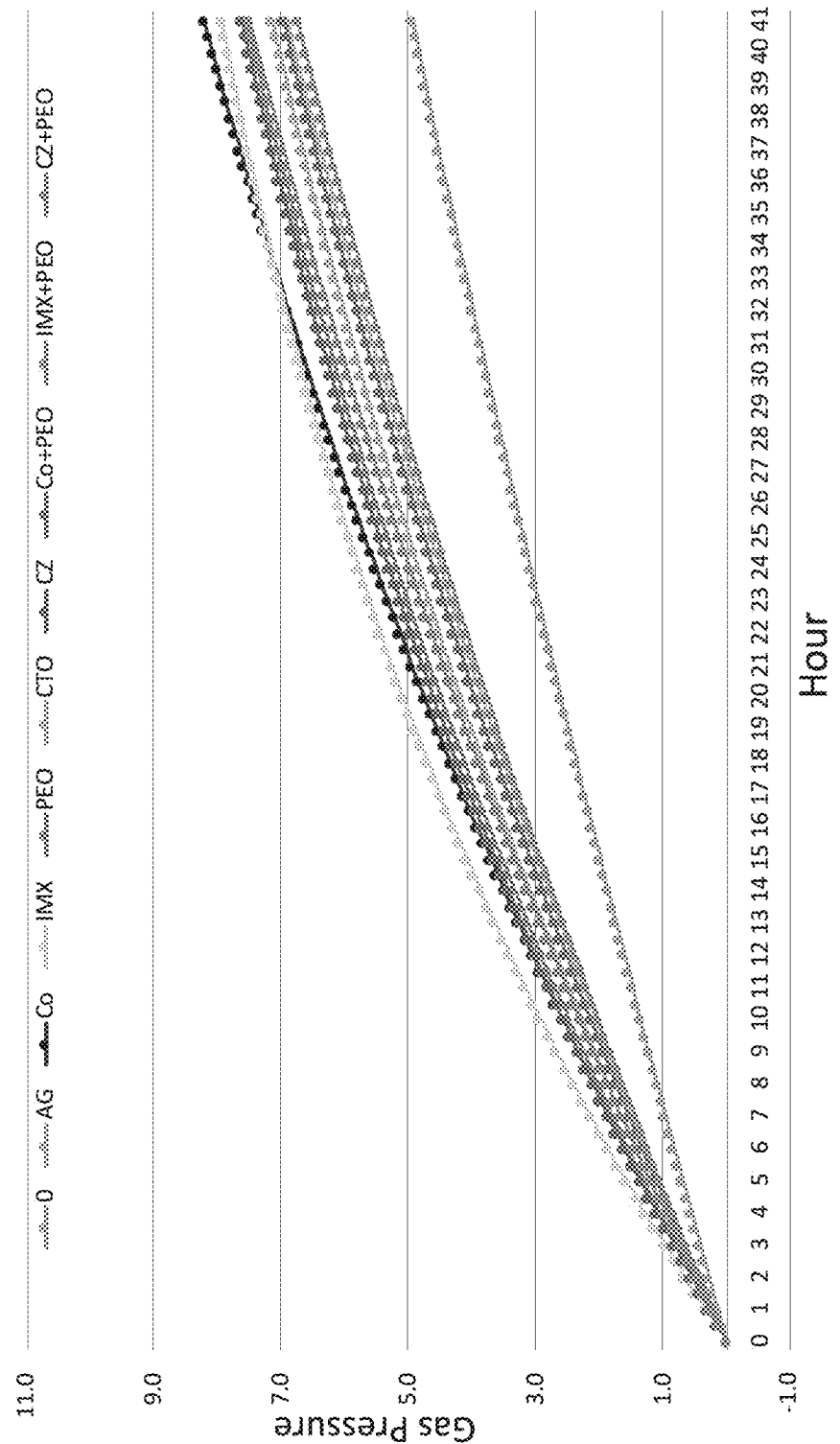
FIG. 6 is a graphical view of gas production for various formulations, according to one or more embodiments of the invention.

The study involved 9 different treatments with three bottles per treatment. Each individual bottle contained a feed sample, a buffer, a rumen fluid, and one of the formulations 0 to 9. Over the course of about 41 hours, the rate and extent of gas production was measured to obtain data representing the extent of digestion, the extent of gas production, the rate of gas production, total gas production, dry matter digestibility, fiber digestibility, and gas production per those units, among other things. The study was designed to permit determination of whether the formulations increased the rate of digestion, among other things. In addition, the study called for measuring volatile fatty acids produced and the influence of the formulations on microbial fermentation. Furthermore, the concentration of ammonia was measured as well. Ruminal ammonia concentration is an indirect measure of microbial protein synthesis. Generally, as was observed, lower ammonia concentrations may mean that more of it is captured as microbial protein. Other measurements included the mL of gas produced, the amount of gas produced per 100 grams of dry matter, or 100 grams of digestible dry matter. The formulations can also have an impact on fiber digestion and so NDF and NDF digestion was also evaluated. Data corresponding to these measurements are presented in the tables below. FIG. 6 is a graphical view of gas production for the various formulations.

TABLE 2

Gas production coefficients, digestibility, pH, and ammonia concentrations for Control (0) and treatments 1 through 9.

| Parameter | Treatments | | | | | | | | | | | F test < |
|---|---|---|---|---|---|---|---|---|---|---|---|---|
| | 0 | 1 | 2 | 3 | 4 | 5 | 6 | 7 | 8 | 9 | SEM | |
| b, potential psi | 18.5$^a$ | 13.1$^b$ | 15.9$^b$ | 11.1$^b$ | 13.0$^b$ | 16.2$^b$ | 12.4$^b$ | 14.6$^b$ | 15.4$^b$ | 15.5$^b$ | 5.98 | 0.39 |
| C, %/hr | 0.76$^c$ | 1.93$^b$ | 1.77$^b$ | 3.06$^a$ | 2.13$^b$ | 1.35$^{bc}$ | 2.32$^{ab}$ | 1.59$^{bc}$ | 1.40$^{bc}$ | 1.62$^b$ | 0.32 | 0.05 |
| Gas, mL | 173.0 | 173.2 | 178.5 | 204.0 | 173.19 | 167.3 | 186.9 | 165.6 | 184.7 | 145.1 | 13.39 | 0.23 |
| Gas, mL/100 g | 8.50$^{ab}$ | 8.56$^{ab}$ | 8.80$^{ab}$ | 10.1$^a$ | 8.63$^{ab}$ | 8.27$^{ab}$ | 9.22$^{ab}$ | 8.16$^{ab}$ | 9.16$^{ab}$ | 7.20$^b$ | 0.64 | 0.21 |
| Gas, mL/100 g DMD | 21.6$^b$ | 22.3$^b$ | 44.1$^a$ | 24.2$^b$ | 20.3$^b$ | 24.1$^b$ | 33.9$^{ab}$ | 23.3$^b$ | 26.4$^{ab}$ | 23.8$^b$ | 3.72 | 0.01 |
| Gas, mL/NDF, g | 14.0$^{ab}$ | 14.1$^{ab}$ | 14.5$^a$ | 16.6$^{ab}$ | 14.2$^{ab}$ | 13.6$^{ab}$ | 15.2$^{ab}$ | 13.4$^{ab}$ | 15.1$^{ab}$ | 11.9$^b$ | 1.05 | 0.21 |
| Gas, mL/NDFd, g | 39.3$^b$ | 39.6$^b$ | 50.8$^a$ | 45.1$^{ab}$ | 36.2$^b$ | 39.0$^b$ | 48.4$^{ab}$ | 39.3$^b$ | 40.9$^b$ | 30.9$^b$ | 4.00 | 0.01 |
| DMD, % | 39.4$^{ab}$ | 37.1$^b$ | 24.9$^c$ | 35.6$^b$ | 42.5$^a$ | 34.2$^{bc}$ | 29.0$^c$ | 36.4$^b$ | 40.9$^{ab}$ | 38.0$^{ab}$ | 3.14 | 0.01 |
| NDFD, % | 35.6$^{ab}$ | 36.5$^{ab}$ | 30.5$^c$ | 34.6$^b$ | 39.2$^a$ | 34.8$^b$ | 32.5$^{bc}$ | 34.2$^b$ | 38.7$^a$ | 37.7$^a$ | 1.34 | 0.01 |
| pH | 6.47$^b$ | 6.48$^b$ | 6.46$^b$ | 6.51$^{ab}$ | 6.46$^b$ | 6.47$^b$ | 6.48$^b$ | 6.54$^a$ | 6.52$^{ab}$ | 6.47$^b$ | 0.018 | 0.06 |
| Ammonia, mg/dL | 28.9$^c$ | 30.3$^b$ | 29.2$^{bc}$ | 30.6$^{ab}$ | 31.5$^a$ | 29.3$^{bc}$ | 29.9$^{bc}$ | 30.4$^{ab}$ | 30.2$^b$ | 28.7$^c$ | 0.633 | <0.05 |

$^{a,b,c,d}$Means within the same row with unlike superscripts differ, P < 0.10.

TABLE 3

Volatile fatty acids for Control (0) and treatments 1 through 9.

| Parameter | Treatments | | | | | | | | | | | F test, < |
|---|---|---|---|---|---|---|---|---|---|---|---|---|
| | 0 | 1 | 2 | 3 | 4 | 5 | 6 | 7 | 8 | 9 | SEM | |
| Acetate, mM | 45.8$^{bc}$ | 44.2$^c$ | 44.6$^c$ | 45.2$^{bc}$ | 48.8$^a$ | 47.1$^{ab}$ | 48.6$^a$ | 47.5$^a$ | 43.5$^c$ | 43.4$^c$ | 1.09 | 0.01 |
| Propionate, mM | 24.5$^b$ | 23.6$^b$ | 24.0$^b$ | 24.4$^b$ | 25.8$^a$ | 25.4$^a$ | 25.9$^a$ | 25.6$^a$ | 23.8$^b$ | 23.4$^c$ | 0.49 | 0.01 |
| Isobutyrate, mM | 1.76$^c$ | 1.76$^c$ | 1.82$^{bc}$ | 1.83$^{bc}$ | 1.88$^{ab}$ | 1.83$^{abc}$ | 1.93$^a$ | 1.86$^{ab}$ | 1.63$^c$ | 1.66$^c$ | 0.06 | 0.03 |
| Butyrate, mM | 10.8$^{abc}$ | 10.5$^c$ | 10.8$^{bc}$ | 10.7$^c$ | 10.9$^{abc}$ | 11.1$^{abc}$ | 11.4$^a$ | 11.4$^a$ | 10.8$^{abc}$ | 10.2$^c$ | 0.31 | 0.07 |
| Isovalerate, mM | 2.94$^c$ | 3.05$^b$ | 3.07$^{ab}$ | 3.14$^{ab}$ | 3.13$^{ab}$ | 3.07$^{ab}$ | 3.21$^a$ | 3.08$^{ab}$ | 2.65$^c$ | 2.76$^c$ | 0.12 | 0.01 |
| Valerate, mM | 3.25$^b$ | 3.36$^{ab}$ | 3.37$^a$ | 3.37$^a$ | 3.44$^a$ | 3.33$^{ab}$ | 3.42$^a$ | 3.36$^a$ | 2.93$^b$ | 2.99$^b$ | 0.11 | 0.02 |
| Total VFA, mM | 89.0$^{bc}$ | 86.5$^c$ | 87.6$^c$ | 88.7$^{bc}$ | 93.9$^a$ | 91.9$^{ab}$ | 94.5$^a$ | 92.7$^a$ | 85.3$^c$ | 84.4$^c$ | 2.07 | 0.01 |
| Molar % | | | | | | | | | | | | |
| Acetate | 51.5$^{ab}$ | 51.0$^{bc}$ | 50.9$^c$ | 50.9$^c$ | 51.9$^a$ | 51.3$^b$ | 51.4$^b$ | 51.2$^{bc}$ | 51.0$^c$ | 51.4$^b$ | 0.19 | 0.01 |
| Propionate | 27.5 | 27.3 | 27.4 | 27.6 | 27.5 | 27.7 | 27.5 | 27.6 | 28.0 | 27.8 | 0.18 | 0.14 |
| Isobutyrate | 1.98$^b$ | 2.03$^b$ | 2.08$^a$ | 2.07$^a$ | 2.00$^b$ | 2.00$^b$ | 2.04$^{ab}$ | 2.00$^b$ | 1.90$^b$ | 1.96$^b$ | 0.04 | 0.0 |
| Butyrate | 12.1$^b$ | 12.2$^{ab}$ | 12.3$^{ab}$ | 12.1$^b$ | 11.6$^c$ | 12.1$^b$ | 12.0$^b$ | 12.3$^{ab}$ | 12.7$^a$ | 12.0$^{bc}$ | 0.18 | 0.01 |
| Isovalerate | 3.30$^c$ | 3.53$^{ab}$ | 3.51$^{ab}$ | 3.54$^a$ | 3.34$^c$ | 3.34$^{bc}$ | 3.39$^{bc}$ | 3.32$^c$ | 3.08$^c$ | 3.25$^c$ | 0.09 | 0.01 |
| Valerate | 3.65$^b$ | 3.88$^a$ | 3.85$^a$ | 3.80$^a$ | 3.67$^b$ | 3.62$^b$ | 3.63$^b$ | 3.62$^b$ | 3.42$^b$ | 3.54$^b$ | 0.07 | 0.01 |
| Acetate/propionate | 1.87$^b$ | 1.87$^b$ | 1.86$^b$ | 1.85$^b$ | 1.89$^a$ | 1.85$^b$ | 1.87$^b$ | 1.86$^b$ | 1.82$^b$ | 1.85$^b$ | 0.01 | 0.01 |

$^{a,b,c}$Means within the same row with different superscripts differ, P < 0.10.
Treatments 8 & 9 demonstrated the most variation in VFA's concentrations.

Example 3

A formulation of a feed additive composition was prepared to evaluate the formulation's ability to increase milk production in a dairy herd of at least 200 cows. The formulation was a combination of cobalt lactate and yeast, and each of the cows were given seven (7) grams of the feed additive once a day for fourteen (14) days. The formulation included between 6.7 and 6.8 grams of yeast (Emprove MX from Emmert) and 150 mg of cobalt lactate (Microbial Catalyst® from Ralco); this formulation is referred to herein as Formulation A. The formulation also included mineral oil for dedusting.

The study was an off, on, off sequence of comparing milk production pre-treatment (off), during treatment (on) and post-treatment (off). Table 4 shows milk production treatment with the formulation compared to milk production pre-treatment and post treatment.

TABLE 4

Milk production and composition for cows pre-treatment, during treatment and after treatment.

| | Treatments | | | |
|---|---|---|---|---|
| Measurement | Pre/Post | Formulation | SEM | P < |
| Milk, lb/d, start | 69.3 | 72.7 | 1.39 | 0.02 |
| Milk, lb/d, end | 78.4 | 80.0 | 0.70 | 0.071 |
| Fat, % | 3.53 | 3.55 | 0.02 | 0.27 |
| Protein, % | 3.11 | 3.12 | 0.01 | 0.12 |
| MUN, mg/dL | 10.80 | 10.82 | 0.04 | 0.81 |
| SCC, x1000 cells | 402.2 | 370.7 | 5.50 | 0.01 |
| DMI, lb/d | 50.7 | 49.0 | 3.36 | 0.72 |

Milk yield was tested using DIM as a covariate, but eliminated from model.

Figure 7:
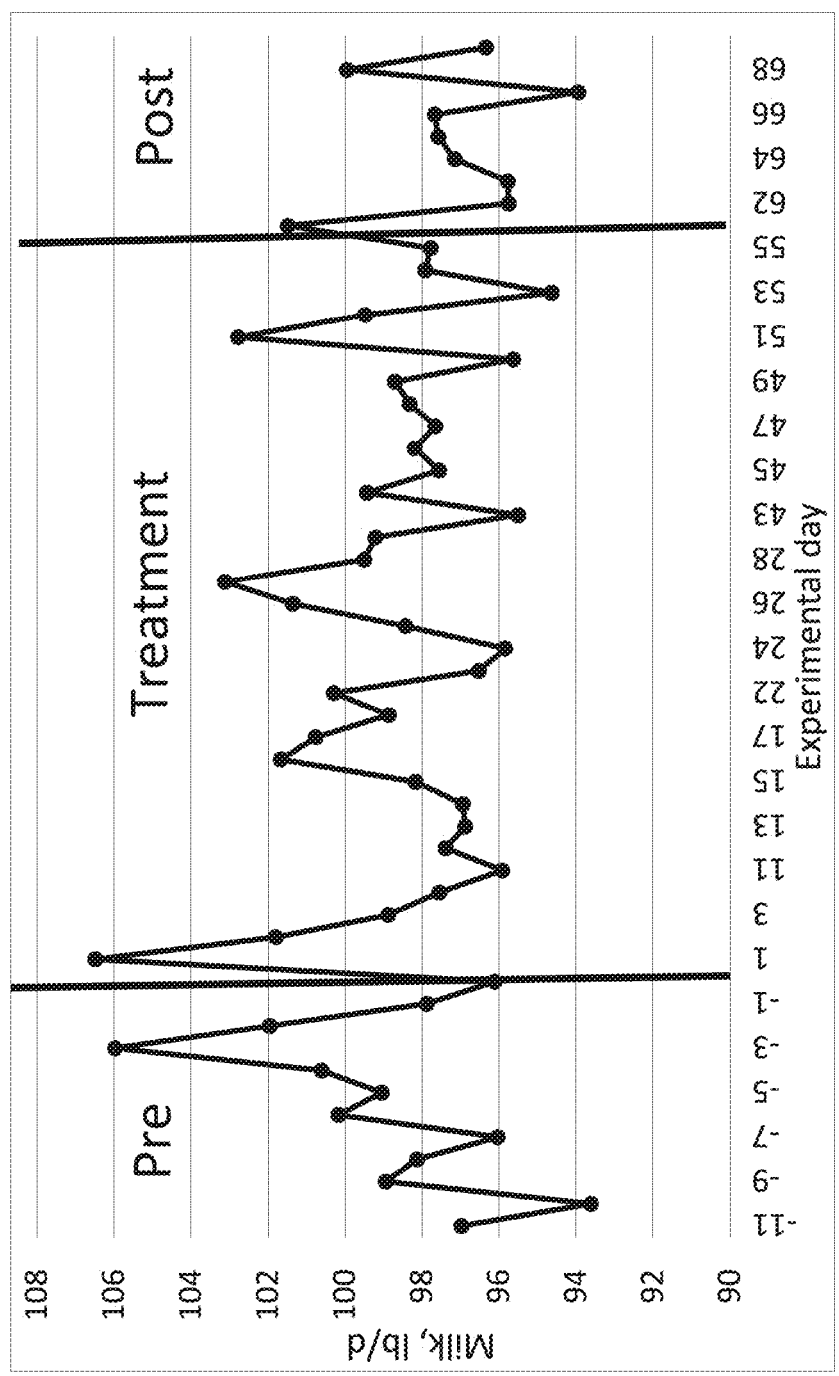
FIG. 7 is a graphical view comparing milk production to when the ruminants are on and off a formulation of yeast and cobalt lactate, according to one or more embodiments of the invention.

Milk production at the start of the trial, using data from −11 to −1 compared with data from 1 to 14 days was increased by 3.4 lb/cow/d (P<0.02) for cows fed Formulation A. Milk production from the end of the trial (last 14 days) compared with 12 days post trial demonstrated a decrease of 1.6 lb/cow/d. Note that twelve days may not have been sufficient for cows to revert to normal production and there may have been a carryover effect of the treatment. FIG. 7 illustrates milk production during pre-treatment, treatment and post-treatment.

Figure 8:
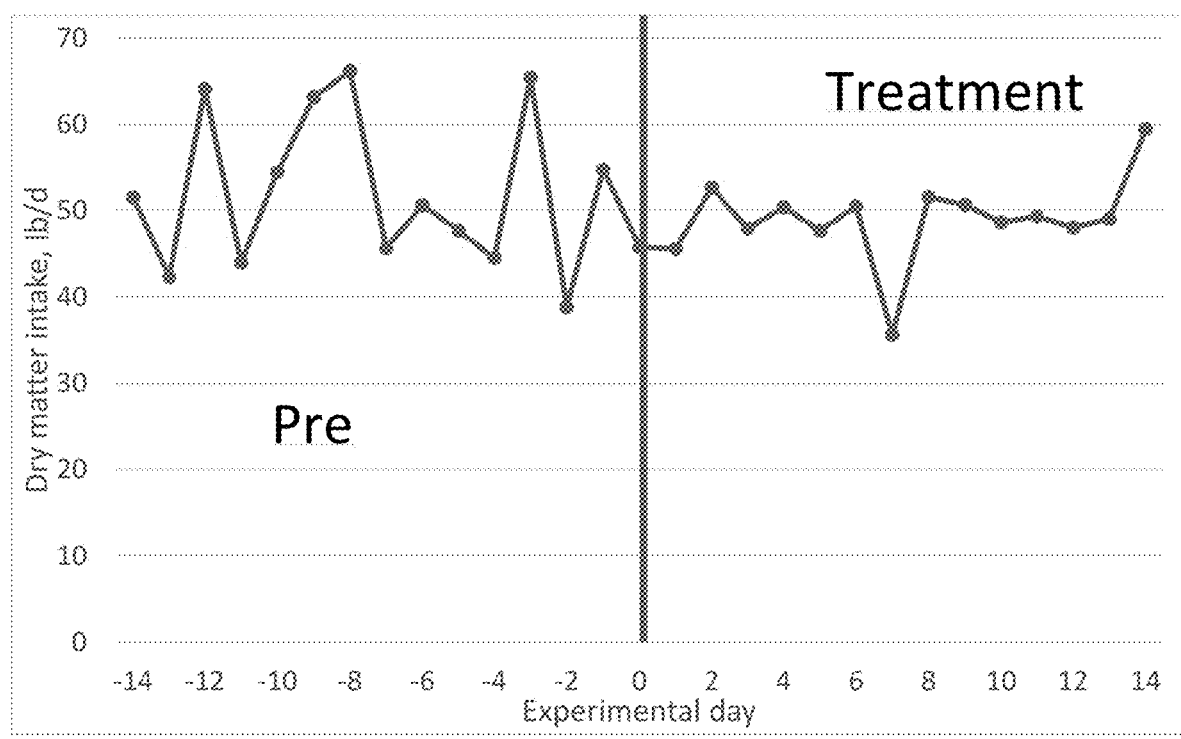
FIG. 8 is a graphical view of dry matter intake before and during treatment of the formulation of yeast and cobalt lactate, according to one or more embodiments of the invention.

No differences were observed in milk composition due to the treatment, based on DHIA data, i.e. fat, protein, and milk urea nitrogen. Somatic cell counts were significantly decreased (P<0.01) with feeding cows the formulation. The data was log transformed and the significance remained. Dry matter intake was numerically lower, but statistically similar for cows fed the formulation as compared to pre or post treatment of the formulation. A more stable dry matter intake from day to day was observed when feeding the formulation, as shown in FIG. 8.

Feed efficiency, based on calculation of Milk/DMI, is 1.55 for cows without treatment, compared to 1.63 for cows treated with the formulation. This difference would be expected to be significant.

In conclusion, this study demonstrated that feeding lactating dairy cows the formulation of cobalt lactate and yeast increased milk production and feed efficiency, while reducing somatic cell counts.

Example 4

Another study was conducted, similar to that of Example 2, to further evaluate the impact of a feed additive composition on milk production for a herd. An off, on cycle of treatment was repeated over a number of days to compare milk productive with the formulation and without. The same formulation from Example 3 (Formulation A) was given to each of the cows as a feed additive once per day.

Table 5 shows the average daily milk production by the herd for the off cycles and the on cycles. The cows produced over two pounds more when the treatment was given as compared to no treatment. The results also show that the composition of the milk in terms of fat, protein and lactose was unaffected by the feed additive/Formulation A.

TABLE 5

Milk production and composition for on and off cycles of treatment

| Cycle | Avg Milk (lbs) | Avg Milk (kilograms) | % fat | % protein | % lactose |
|---|---|---|---|---|---|
| OFF (no treatment) | 71.9 | 32.6 | 4.43 | 3.54 | 4.56 |
| ON (with treatment) | 74.1 | 33.6 | 4.38 | 3.58 | 4.56 |

Figure 9:
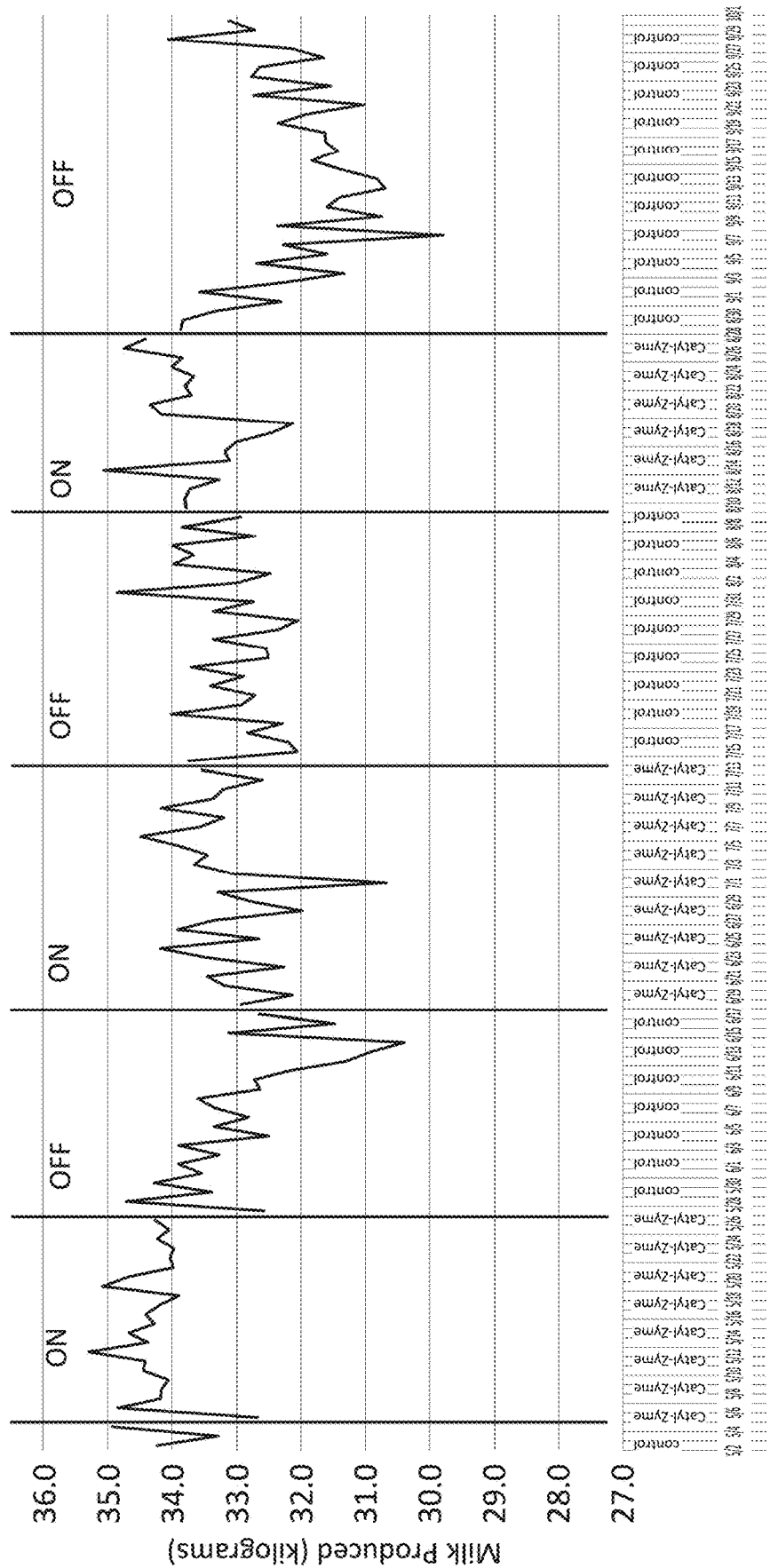
FIG. 9 is a graphical view comparing milk production when ruminants are cycling on and off a formulation of yeast and cobalt lactate, according to one or more embodiments of the invention.

FIG. 9 is a graph of daily milk production (in kilograms) for the herd with the off and on cycles identified on the graph. As demonstrated by FIG. 9, a decline in milk production was generally observed as the off cycle proceeded, followed by an increase in milk production as the treatment resumed.

Example 5

This study was conducted to evaluate the feed additive composition in an ANKOM artificial rumen system to compare digestibility of a feed additive of a cobalt lactate/yeast blend, relative to a feed additive of only cobalt lactate and a feed additive of only yeast. In each run, two cannulated steers were used to collect rumen fluid from the two steers at the Ralco Beef Research Farm in Marshall, MN. The rumen fluid was mixed with a buffer solution along with a different feed additive composition in each of three jars and a fourth jar having a control with no treatment. Eight runs were performed at differing amounts of cobalt lactate, yeast, and blends of cobalt lactate and yeast, as shown in each of the tables below. The cobalt lactate used in Runs 1-8 was Microbial Catalyst® from Ralco. The yeast used in Runs 1-8 was Emprove MX from Emmert.

Dacron bags with hay (Barley straw, DM 94.2, CP 5.4, ADF 54.15, NDF 75.6, Neg/cwt 17.7 and Nem/cwt 42.5 respectively) samples were then added to each jar, the jar was purged with $CO_2$ and incubated for 24 hours at 39.5 degrees C. At the end of the 24 hours, the bags were removed, washed with clear tap water and run through the ANKOM fiber analyzer. At that point, the bags were dried and re-weighed, and the weight entered into formulas to give a dry matter digestibility value.

Run 1:

TABLE 6

Compositions and Results from Run 1

| Treatment | Composition | DMD | SEM | g/hd/d[1] |
|---|---|---|---|---|
| Control | No treatment | 50.13$^a$ | 0.27 | 0 |
| 1 | 3.0 g cobalt lactate | 54.37$^b$ | 0.38 | 136.38 |
| 2 | 3.0 g yeast | 51.50$^c$ | 0.38 | 136.38 |
| 3 | 6.0 g blend (3.0 g cobalt lactate + 3.0 g yeast) | 56.08$^d$ | 0.38 | 272.74 |

$^{a,b,c}$DMD value with different superscripts differ (P < .05)
[1]Calculated theoretical supplement per head daily All treatments showed a higher dry matter disappearance as compared to the control. Treatments 1 and 3 were significantly higher than treatment two, and treatment three had the highest digestibility value.

All treatments showed a higher dry matter disappearance as compared to the control. Treatments 1 and 3 were significantly higher than treatment two, and treatment three had the highest digestibility value.

Run 2:

TABLE 7

Compositions and Results from Run 2

| Treatment | Composition | DMD | SEM | g/hd/d[1] |
|---|---|---|---|---|
| Control | No treatment | 52.62$^a$ | 0.33 | 0 |
| 1 | 6.0 g cobalt lactate | 57.04$^b$ | 0.47 | 272.74 |
| 2 | 6.0 g yeast | 53.99$^c$ | 0.47 | 272.74 |
| 3 | 12.0 g blend (6.0 g cobalt lactate + 6.0 g yeast) | 61.53$^d$ | 0.47 | 545.46 |

$^{a,b,c}$DMD value with different superscripts differ (P < .05)
[1]Calculated theoretical supplement per head daily All treatments showed a higher dry matter disappearance as compared to the control. Treatments 1 and 3 were significantly higher than treatment two, and treatment three had the highest digestibility value.

Run 3:

TABLE 8

Compositions and Results from Run 3

| Treatment | Composition | DMD | SEM | g/hd/d[1] |
|---|---|---|---|---|
| Control | No treatment | 51.11$^a$ | 0.33 | 0 |
| 1 | 3.0 g cobalt lactate | 61.87$^b$ | 0.46 | 136.38 |
| 2 | 6.0 g yeast | 54.62$^c$ | 0.46 | 272.74 |
| 3 | 9.0 g blend (3.0 g cobalt lactate + 6.0 g yeast) | 60.80$^d$ | 0.46 | 409.10 |

$^{a,b,c}$DMD value with different superscripts differ (P < .05)
[1]Calculated theoretical supplement per head daily All treatments showed a higher dry matter disappearance compared to the control. Treatment one was higher than treatments two or three. Treatment three was significantly higher when compared to treatment two.

Run 4:

TABLE 9

Compositions and Results from Run 4

| Treatment | Composition | DMD | SEM |
|---|---|---|---|
| Control | No treatment | 53.37$^a$ | 0.32 |
| 1 | 3.0 g cobalt lactate | 61.83$^c$ | 0.45 |
| 2 | 6.0 g yeast | 54.09$^a$ | 0.45 |
| 3 | 6.0 g blend (3.0 g cobalt lactate + 3.0 g yeast) | 60.58$^b$ | 0.45 |

$^{a,b,c}$DMD value with different superscripts differ (P < .05)

All treatments were higher than the control. There was no significant difference between treatment two and the control. Treatments one and three were significantly higher in dry matter disappearance compared to the control.

Run 5:

Run 5 was a repeat of the treatments tested in Run 4.

TABLE 10

Compositions and Results from Run 5

| Treatment | Composition | DMD | SEM |
|---|---|---|---|
| Control | No treatment | 53.92$^a$ | 0.28 |
| 1 | 3.0 g cobalt lactate | 64.59$^c$ | 0.39 |
| 2 | 6.0 g yeast | 53.65$^a$ | 0.39 |
| 3 | 6.0 g blend (3.0 g cobalt lactate + 3.0 g yeast) | 58.90$^b$ | 0.39 |

$^{a,b,c}$DMD value with different superscripts differ (P < .05)

Treatments one and three were significantly higher in dry matter disappearance compared to the control. There was no significant difference between treatment two and the control.

Run 6:

Similar to Runs 1-5, Runs 6-8 contained a blend of cobalt lactate and yeast (Treatment 1). However, in Runs 6-8, the blend was Formulation A provided above in Example 3.

TABLE 11

Compositions and Results from Run 6

| Treatment | Composition | DMD |
|---|---|---|
| Control | No treatment | 59.40$^b$ |
| 1 | 7.0 g Formulation A | 65.51$^d$ |
| 2 | 6.5 g yeast | 56.30$^a$ |
| 3 | 3.0 g cobalt lactate | 62.41$^c$ |

$^{a,b,c}$DMD value with different superscripts differ (P < .05)

Treatment two showed lower dry matter disappearance than the control, while treatments one and three were significantly higher. Formulation A of cobalt lactate and yeast showed the highest dry matter disappearance.

Run 7:

Run 7 was a repeat of Run 6.

TABLE 12

Compositions and Results from Run 7

| Treatment | Composition | DMD |
|---|---|---|
| Control | No treatment | 58.95$^a$ |
| 1 | 7.0 g Formulation A | 66.76$^c$ |
| 2 | 6.5 g yeast | 59.26$^a$ |
| 3 | 3.0 g cobalt lactate | 62.17$^b$ |

$^{a,b,c}$DMD value with different superscripts differ (P < .05)

Similar results were shown as compared to Run 6, except that treatment two had higher dry matter disappearance than the control. Treatment one was significantly higher than the control and other treatments.

Run 8:

Run 8 was also a repeat of Run 6.

TABLE 13

Compositions and Results from Run 8

| Treatment | Composition | DMD |
|---|---|---|
| Control | No treatment | 57.95$^a$ |
| 1 | 7.0 g Formulation A | 70.31$^d$ |
| 2 | 6.5 g yeast | 59.17$^b$ |
| 3 | 3.0 g cobalt lactate | 66.71$^c$ |

$^{a,b,c}$DMD value with different superscripts differ (P < .05)

Similar results were shown compared to Run 7, including treatment one having the highest dry matter disappearance.

Runs 1-8 demonstrated that a blend of cobalt lactate and yeast resulted in higher digestibility, as compared to using cobalt lactate or yeast alone.

Example 6

In this study a similar analysis was performed as in Example 5. In this example, Formulation A (used in Runs 6-8) was compared to Product 1 (Diamond V XPC®) and Product 2 (Amaferm® from BioZyme). The protocol used in this example is the same as that provided above for Example 5.

Run 9:

TABLE 14

Compositions and Results from Run 9

| Treatment | Composition | DMD | SEM |
|---|---|---|---|
| Control | No treatment | 57.09$^a$ | 0.358 |
| 1 | 7.0 g Formulation A | 61.95$^c$ | 0.358 |
| 2 | 7.0 g Product 1 | 58.25$^b$ | 0.358 |
| 3 | 3.0 g Product 2 | 57.13$^a$ | 0.358 |

$^{a,b,c}$DMD value with different superscripts differ (P < .05)

All treatments had higher digestibility than the control. There was no statistical difference between the control and Treatment 3 (Product 2). Treatment 1 had higher digestibility than the control and Products 1 and 2.

Run 10:

TABLE 15

Compositions and Results from Run 10

| Treatment | Composition | DMD | SEM |
|---|---|---|---|
| Control | No treatment | 55.60$^a$ | 0.344 |
| 1 | 7.0 g Formulation A | 61.06$^c$ | 0.344 |

TABLE 15-continued

Compositions and Results from Run 10

| Treatment | Composition | DMD | SEM |
|---|---|---|---|
| 2 | 7.0 g Product 1 | 58.85[b] | 0.344 |
| 3 | 3.0 g Product 2 | 56.28[a] | 0.344 |

[a,b,c]DMD value with different superscripts differ (P < .05)

All treatments had higher digestibility than the control. Treatment 1 had higher digestibility than control and the other 2 treatments.

Run 11:

TABLE 16

Compositions and Results from Run 11

| Treatment | Composition | DMD | SEM |
|---|---|---|---|
| Control | No treatment | 56.83[a] | 0.501 |
| 1 | 7.0 g Formulation A | 60.91[b] | 0.501 |
| 2 | 7.0 g Product 1 | 58.12[a] | 0.501 |
| 3 | 3.0 g Product 2 | 57.45[a] | 0.501 |

[a,b,c]DMD value with different superscripts differ (P < .05)

All treatments had higher digestibility than the control. Treatment 1 had higher digestibility than control and the other 2 treatments.

Run 12:

TABLE 17

Compositions and Results from Run 12

| Treatment | Composition | DMD | SEM |
|---|---|---|---|
| Control | No treatment | 56.74[b] | 0.352 |
| 1 | 7.0 g Formulation A | 60.42[c] | 0.352 |
| 2 | 7.0 g Product 1 | 55.46[a] | 0.352 |
| 3 | 5.0 g Product 2 | 54.65[a] | 0.352 |

[a,b,c]DMD value with different superscripts differ (P < .05)

Product 2 (which was at a higher amount (5.0 g) compared to Runs 9-11 (3.0 g)) had the lowest digestibility, followed by Product 1. The control had higher digestibility than both Products 1 and 2. Treatment 1 was significantly higher than any of the other treatments.

Run 13: Run 13 was a repeat of the treatments tested in Run 12.

TABLE 18

Compositions and Results from Run 13

| Treatment | Composition | DMD | SEM |
|---|---|---|---|
| Control | No treatment | 55.35[a] | 0.256 |
| 1 | 7.0 g Formulation A | 60.85[c] | 0.256 |
| 2 | 7.0 g Product 1 | 55.97[a] | 0.256 |
| 3 | 5.0 g Product 2 | 56.97[b] | 0.256 |

[a,b,c]DMD value with different superscripts differ (P < .05)

Although in this run Product 2 had higher digestibility compared to Product 1 and the Control, the results are similar to Run 12. Treatment 1 (Formulation A) was significantly higher than any of the other treatments.

Run 14:
Run 14 was also a repeat of Run 12.

TABLE 19

Compositions and Results from Run 14

| Treatment | Composition | DMD | SEM |
|---|---|---|---|
| Control | No treatment | 56.36[a] | 0.499 |
| 1 | 7.0 g Formulation A | 60.45[b] | 0.499 |
| 2 | 7.0 g Product 1 | 55.73[a] | 0.499 |
| 3 | 5.0 g Product 2 | 55.78[a] | 0.499 |

[a,b,c]DMD value with different superscripts differ (P < .05)

This run produced similar results. Treatment 1 (Formulation A) had the higher digestibility.

Run 15:

In Run 15, a higher amount of the treatment was used. Treatment 1 was a 14 gram blend of cobalt lactate and yeast. Treatment 1 was 13.5 grams of yeast and 60 mg of cobalt lactate (Microbial Catalyst®); this formulation is referred to herein as Formulation B. The treatments of Run 15 were also repeated in Runs 16-20, included below.

TABLE 20

Compositions and Results from Run 15

| Treatment | Composition | DMD | SEM |
|---|---|---|---|
| Control | No treatment | 54.43[a] | 0.29 |
| 1 | 14.0 g Formulation B | 61.95[d] | 0.29 |
| 2 | 14.0 g Product 1 | 60.47[c] | 0.29 |
| 3 | 10.0 g Product 2 | 58.42[b] | 0.29 |

[a,b,c]DMD value with different superscripts differ (P < .05)

All groups were statistically different from one another. All treatments had higher digestibility than the control. Treatment 1 (Formulation B) had the highest digestibility.

Run 16:

TABLE 21

Compositions and Results from Run 16

| Treatment | Composition | DMD | SEM |
|---|---|---|---|
| Control | No treatment | 52.90[a] | 0.26 |
| 1 | 14.0 g Formulation B | 66.62[c] | 0.26 |
| 2 | 14.0 g Product 1 | 56.05[b] | 0.26 |
| 3 | 10.0 g Product 2 | 55.62[b] | 0.26 |

[a,b,c]DMD value with different superscripts differ (P < .05)

Treatments 2 and 3 were not statistically different. Treatment 1 (Formulation B) had significantly higher digestibility than all others.

Run 17:

TABLE 22

Compositions and Results from Run 17

| Treatment | Composition | DMD | SEM |
|---|---|---|---|
| Control | No treatment | 53.74[a] | 1.41 |
| 1 | 14.0 g Formulation B | 60.70[b] | 1.41 |
| 2 | 14.0 g Product 1 | 58.65[b] | 1.41 |
| 3 | 10.0 g Product 2 | 58.20[b] | 1.41 |

[a,b,c]DMD value with different superscripts differ (P < .05)

Treatments 1-3 had similar digestibility, and none were statistically different. Treatments 1-3 had higher digestibility than the control.

Run 18:

TABLE 23

Compositions and Results from Run 18

| Treatment | Composition | DMD | SEM |
|---|---|---|---|
| Control | No treatment | 56.59[a] | 0.41 |
| 1 | 14.0 g Formulation B | 64.68[d] | 0.41 |
| 2 | 14.0 g Product 1 | 61.71[c] | 0.41 |
| 3 | 10.0 g Product 2 | 58.37[b] | 0.41 |

[a,b,c]DMD value with different superscripts differ (P < .05)

Treatments 1-3 had higher digestibility than the control and all were statistically different. Treatment 1 (Formulation B) had the highest digestibility.

Run 19:

TABLE 24

Compositions and Results from Run 19

| Treatment | Composition | DMD | SEM |
|---|---|---|---|
| Control | No treatment | 54.12[a] | 0.25 |
| 1 | 14.0 g Formulation B | 63.34[d] | 0.25 |
| 2 | 14.0 g Product 1 | 58.72[c] | 0.25 |
| 3 | 10.0 g Product 2 | 56.54[b] | 0.25 |

[a,b,c]DMD value with different superscripts differ (P < .05)

Similar to the results in Run 18, Treatments 1-3 had higher digestibility than the control and all were statistically different. Treatment 1 (Formulation B) had significantly higher digestibility than Treatments 2 and 3.

Run 20:

TABLE 25

Compositions and Results from Run 20

| Treatment | Composition | DMD | SEM |
|---|---|---|---|
| Control | No treatment | 54.76[a] | 0.28 |
| 1 | 14.0 g Formulation B | 63.07[d] | 0.28 |
| 2 | 14.0 g Product 1 | 57.96[c] | 0.28 |
| 3 | 10.0 g Product 2 | 57.12[b] | 0.28 |

[a,b,c]DMD value with different superscripts differ (P < .05)

Run 20 had similar results to Runs 18 and 19. Treatment 1 (Formulation B) had the highest digestibility.

The results of Runs 9-20 show that Formulations A and B, both of which are a blend of yeast and cobalt lactate, performed better than if no additive treatment was provided. Moreover, Formulations A and B were shown to perform better than Products 1 and 2.

Example 7

This study was conducted to evaluate and determine the impact on eight (8) week old calves that were given the blended formulation of yeast and cobalt. The blended formulation was compared to a control and another product and evaluated in terms of body weight gain, dry matter intake, feed conversions, and ruminal and metabolic parameters. Treatment 1 was a control of mini-pelleted 18% CP complete grain mix (without yeast or cobalt). Treatment 2 was another product, Ultra XP yeast (Diamond V®), fed at a rate of 3.5 g/steer/day. Treatment 3 was a blended formulation of cobalt lactate and yeast fed at a rate of 3.5 g/steer/day.

The blended formulation used in Treatment 3 included 3.4 grams of yeast and 75 mg of cobalt lactate (Microbial Catalyst®); this formulation is referred to herein as Formulation C. Cobalt carbonate at 0.2 ppm (NRC) was added to each of Treatments 1-3. The experimental design was a randomized complete block design with the three treatments. Calves were blocked by body weight, and initial body weight was tested as a covariate. If P>0.15 for the covariate, it was dropped from the model.

Grain mix was fed at 5 lb/steer/day and alfalfa hay was fed free choice with amounts fed and refusals recorded daily. Pellets were 5/32 in size. The treatments were added to the grain mix such that the treatments were part of the feed to the steer. The three treatments were kept in separate bags of differing colors with tags of differing colors.

The steer were housed in a Agri-Plastics or Calf-Tel 86.5"×107.5"×72" super calf hutch to hold 4-6 steers per pen. The pen was bedded with a layer of rice hulls followed by chopped wheat straw to ensure a warm dry clean comfortable bed. Straw bedding was added as needed to keep the animals dry.

The study evaluated 78 Holstein bull calves that were 56 days old (eight weeks) at the start of the study. The calves/steers were coming off a milk replacer trial evaluating a new feed additive to improve fat, energy and digestion. The calves were weighed, frames were measured at the start of the study. The calves were also dehorned and castrated at the start of the study, followed by a one 10 mL dose of Start Strong® from Ralco. Twenty-six (26) steers were assigned to treatment, in groups of 5 or 6 steers per treatment per super hutch.

The experimental period of the study was 12 weeks (84 days). Body weights were collected every two weeks. Frame measurements were collected at 0, 8 and 12 weeks. Fecal grab samples were collected at weeks 8 and 12 for measurement of nutrient digestion. Samples were stored for later determination. Blood samples were collected for blood urea nitrogen at weeks 8 and 12 at 2 to 4 hours after feeding. Rumen fluid samples were collected at weeks 8 and 12 via esophageal suction tube and strainer at 2 to 4 hours after feeding. The pH was immediately checked and if above 7, the fluid was discarded and collected again. Samples were stored for VFA, Ammonia, and Microbial Community Profiles. All treatments and disease incidences were recorded. Calves were given Ultrabac® 7 from Zoetis (5 cc subcutaneous) during week 2 and again 4 weeks later for a booster. The table below shows the experimental timeline and measurements.

TABLE 26

Experimental timeline

| Week/Day | Feeding | BWT & Feed Weights | Steer Body Measurements | Blood & Rumen Samples | Fecal |
|---|---|---|---|---|---|
| Day 1 | Block calves Groups of 5 in Super hutches | X | | | |
| Wk 1 | | | | | |
| Wk 2 | | X | | | |
| Wk 3 | | | | | |
| Wk 4 | | X | | | |
| Wk 5 | | | | | |
| Wk 6 | | X | | | |
| Wk 7 | | | | | |
| Wk 8 | | X | X | X | X |
| Wk 9 | | | | | |
| Wk 10 | | X | | | |
| Wk 11 | | | | | |

TABLE 26-continued

Experimental timeline

| Week/Day | Feeding | BWT & Feed Weights | Steer Body Measurements | Blood & Rumen Samples | Fecal |
|---|---|---|---|---|---|
| Wk 12 Study ends | Wash hutches | X | X | X | X |

Collected measurements and corresponding calculations are shown in Tables 27-33 below. A summary of the results follows the tables.

TABLE 27

Body weight (BW), BW gain, and average daily gains (ADG) for steers fed no yeast (Control/Treatment 1), Treatment 2, and Treatment 3 (Formulation C)

| Measurement | Treatment 1 | 2 | 3 (Form C) | SEM | Contrast, P< 1 | 2 |
|---|---|---|---|---|---|---|
| BW, kg | | | | | | |
| Day 0 | 79.13 | 78.80 | 79.11 | 4.44 | 0.84 | 0.82 |
| Day 14 | 92.31 | 91.39 | 92.23 | | | |
| Day 28 | 110.52 | 109.79 | 110.15 | | | |
| Day 42 | 123.61 | 123.55 | 122.07 | | | |
| Day 56 | 138.75 | 139.38 | 138.73 | | | |
| Day 70 | 150.71 | 153.16 | 152.54 | | | |
| Mean BW, kg | 115.84 | 116.01 | 115.81 | 4.19 | 0.84 | 0.82 |
| BW gain, kg/period | | | | | | |
| Day 14 | 13.2 | 12.6 | 13.2 | 1.41 | 0.88 | 0.68 |
| Day 28 | 18.2 | 18.4 | 17.8 | 1.79 | 0.82 | 0.93 |
| Day 42 | 13.0 | 13.7 | 11.9 | 2.10 | 0.51 | 0.59 |
| Day 56 | 16.3 | 15.8 | 16.6 | 1.39 | 0.28 | 0.66 |
| Day 70 | 12.0 | 13.8 | 13.8 | 2.24 | 0.53 | 0.48 |
| Total BW gain, kg | 71.6 | 74.4 | 73.4 | 1.65 | 0.79 | 0.18 |
| ADG, g/d/period | | | | | | |
| Day 14 | 941.0 | 899.1 | 937.6 | 101.1 | 0.88 | 0.68 |
| Day 28 | 1214.2 | 1226.6 | 1194.5 | 88.6 | 0.82 | 0.93 |
| Day 42 | 1007.3 | 1058.5 | 917.3 | 161.9 | 0.51 | 0.59 |
| Day 56 | 1081.0 | 1131.3 | 1189.8 | 99.29 | 0.28 | 0.66 |
| Day 70 | 854.4 | 984.1 | 986.2 | 159.7 | 0.53 | 0.48 |
| Mean ADG, g/d | 1037.3 | 1077.7 | 1064.3 | 24.0 | 0.79 | 0.18 |

Contrast 1 = Control (Treatment 1) versus Treatments 2 and 3
Contrast 2 = Treatment 2 versus Treatment 3 (Formulation C)

TABLE 28

Hay, grain mix, and total dry matter intake (DMI) for steers fed no yeast (Control/Treatment 1), Treatment 2, and Treatment 3 (Formulation C)

| Measurement | Treatment 1 | 2 | 3 (Form C) | SEM | Contrast, P< 1 | 2 |
|---|---|---|---|---|---|---|
| Hay DMI, kg | | | | | | |
| Day 7 | 0.10 | 0.11 | 0.12 | 0.14 | 0.16 | 0.30 |
| Day 14 | 0.30 | 0.28 | 0.35 | | | |
| Day 21 | 0.66 | 0.74 | 0.81 | | | |
| Day 28 | 0.76 | 0.78 | .79 | | | |
| Day 35 | 1.39 | 1.36 | 1.31 | | | |
| Day 42 | 1.41 | 1.42 | 1.38 | | | |
| Day 49 | 1.65 | 1.67 | 1.65 | | | |
| Day 56 | 1.72 | 1.74 | 1.76 | | | |
| Day 63 | 1.88 | 1.97 | 2.06 | | | |
| Day 70 | 2.26 | 2.42 | 2.47 | | | |
| Mean hay DMI, kg | 1.21 | 1.25 | 1.27 | 0.10 | 0.16 | 0.30 |
| Grain DMI, kg | 2.06 | 2.00 | 2.01 | 0.01 | 0.01 | 0.01 |
| Total DMI, kg/d | | | | | | |
| Day 7 | 1.87 | 1.88 | 1.89 | 0.14 | 0.49 | 0.42 |
| Day 14 | 2.34 | 2.27 | 2.39 | | | |
| Day 21 | 2.70 | 2.77 | 2.85 | | | |
| Day 28 | 2.81 | 2.81 | 2.83 | | | |
| Day 35 | 3.51 | 3.39 | 3.34 | | | |
| Day 42 | 3.53 | 3.45 | 3.41 | | | |
| Day 49 | 3.77 | 3.70 | 3.69 | | | |
| Day 56 | 3.85 | 3.76 | 3.79 | | | |
| Day 63 | 4.00 | 4.00 | 4.09 | | | |
| Day 70 | 4.38 | 4.45 | 4.50 | | | |
| Mean DMI, kg/d | 3.28 | 3.25 | 3.28 | 0.11 | 0.49 | 0.42 |
| DMI/BW, % | | | | | | |
| Day 7 | 2.19 | 2.21 | 2.22 | 0.06 | 0.20 | 0.26 |
| Day 14 | 2.54 | 2.49 | 2.59 | | | |
| Day 21 | 2.66 | 2.75 | 2.81 | | | |
| Day 28 | 2.55 | 2.56 | 2.57 | | | |
| Day 35 | 3.00 | 2.91 | 2.87 | | | |
| Day 42 | 2.86 | 2.80 | 2.80 | | | |
| Day 49 | 2.87 | 2.82 | 2.83 | | | |
| Day 56 | 2.77 | 2.70 | 2.73 | | | |
| Day 63 | 2.76 | 2.73 | 2.81 | | | |
| Day 70 | 2.90 | 2.90 | 2.95 | | | |
| Mean DMI/BW, % | $2.71^{ab}$ | $2.69^{b}$ | $2.72^{a}$ | 0.03 | 0.20 | 0.26 |

[a,b]Means with unlike superscripts differ, $P \leq 0.05$.
Contrast 1 = Control (Treatment 1) versus Treatments 2 and 3
Contrast 2 = Treatment 2 versus Treatment 3 (Formulation C)

TABLE 29

Forage as a % of total dry mater intake for steers fed no yeast (Control/Treatment 1), Treatment 2, and Treatment 3 (Formulation C)

| Measurement | Treatment 1 | 2 | 3 (Form C) | SEM | Contrast, P< 1 | 2 |
|---|---|---|---|---|---|---|
| Forage, % | | | | | | |
| Day 7 | 5.30 | 5.98 | 6.41 | 2.34 | 0.01 | 0.01 |
| Day 14 | 12.45 | 12.40 | 14.31 | | | |
| Day 21 | $23.65^{b}$ | $26.48^{ab}$ | $27.93^{a}$ | | | |
| Day 28 | 26.56 | 27.65 | 27.54 | | | |
| Day 35 | 38.89 | 37.75 | 38.57 | | | |
| Day 42 | 39.71 | 41.07 | 40.18 | | | |
| Day 49 | 43.37 | 45.10 | 44.66 | | | |
| Day 56 | 44.35 | 46.05 | 46.17 | | | |
| Day 63 | $46.42^{b}$ | $49.12^{ab}$ | $50.20^{a}$ | | | |
| Day 70 | $50.86^{b}$ | $54.06^{ab}$ | $54.59^{a}$ | | | |
| Mean Forage, % | $33.3^{b}$ | $34.8^{ab}$ | $35.1^{a}$ | 1.91 | 0.01 | 0.01 |
| Grain cost, $/d | 0.407 | 0.416 | 0.410 | 0.001 | 0.11 | 0.01 |
| Hay cost, $/d | 0.123 | 0.127 | 0.128 | 0.003 | 0.20 | 0.36 |
| Total cost, $/d | 0.528 | 0.541 | 0.536 | 0.003 | 0.59 | 0.01 |

[a,b]Means with unlike superscripts differ, $P \leq 0.05$.
Contrast 1 = Control (Treatment 1) versus Treatments 2 and 3
Contrast 2 = Treatment 2 versus Treatment 3 (Formulation C)

TABLE 30

Feed conversions (gain/dry matter intake: DMI) for steers fed no yeast (Control/Treatment 1), Treatment 2, and Treatment 3 (Formulation C)

|  | Treatment | | | | Contrast, P< | |
|---|---|---|---|---|---|---|
| Measurement | 1 | 2 | 3 (Form C) | SEM | 1 | 2 |
| FC, kg gain/kg DMI | | | | | | |
| Day 7 | 0.506 | 0.485 | 0.501 | 0.02 | 0.48 | 0.88 |
| Day 14 | 0.450 | 0.438 | 0.442 | | | |
| Day 21 | 0.462 | 0.454 | 0.446 | | | |
| Day 28 | 0.462 | 0.458 | 0.448 | | | |
| Day 35 | 0.411 | 0.415 | 0.400 | | | |
| Day 42 | 0.380 | 0.388 | 0.369 | | | |
| Day 49 | 0.364 | 0.373 | 0.361 | | | |
| Day 56 | 0.351 | 0.362 | 0.354 | | | |
| Day 63 | 0.332 | 0.345 | 0.337 | | | |
| Day 70 | 0.313 | 0.328 | 0.321 | | | |
| Mean FC, kg/kg | 0.403 | 0.404 | 0.398 | 0.01 | 0.48 | 0.88 |

Contrast 1 = Control (Treatment 1) versus Treatments 2 and 3
Contrast 2 = Treatment 2 versus Treatment 3 (Formulation C)

TABLE 31

Frame measurements for steers fed no yeast (Control/Treatment 1), Treatment 2, and Treatment 3 (Formulation C)

|  | Treatment | | | | Contrast, P< | |
|---|---|---|---|---|---|---|
| Measurement | 1 | 2 | 3 | SEM | 1 | 2 |
| Body length, cm | | | | | | |
| Initial | 63.3 | 63.6 | 63.3 | 0.46 | 0.83 | 0.65 |
| Final | 76.8$^a$ | 73.9$^b$ | 74.1$^{ab}$ | 0.90 | 0.28 | 0.06 |
| Gain | 13.4$^a$ | 10.3$^b$ | 10.7$^{ab}$ | 1.64 | 0.37 | 0.06 |
| Withers height | | | | | | |
| Initial | 88.6 | 88.0 | 87.0 | 0.63 | 0.13 | 0.92 |
| Final | 98.3 | 98.2 | 97.6 | 0.64 | 0.33 | 0.92 |
| Gain | 9.71 | 10.2 | 10.6 | 0.49 | 0.24 | 0.97 |
| Heart girth | | | | | | |
| Initial | 99.1 | 99.4 | 99.2 | 0.82 | 0.92 | 0.70 |
| Final | 116.0 | 117.5 | 117.3 | 0.59 | 0.45 | 0.14 |
| Gain | 16.9 | 18.1 | 18.1 | 0.44 | 0.27 | 0.11 |
| Hip height | | | | | | |
| Initial | 92.8 | 92.2 | 91.6 | 0.96 | 0.27 | 0.46 |
| Final | 102.7$^b$ | 101.7$^{ab}$ | 101.0$^b$ | 0.97 | 0.18 | 0.34 |
| Gain | 9.91 | 9.49 | 9.46 | 0.87 | 0.98 | 0.83 |
| Hip width | | | | | | |
| Initial | 25.4 | 25.1 | 25.4 | 0.27 | 0.59 | 0.45 |
| Final | 64.4 | 63.7 | 64.5 | 0.69 | 0.59 | 0.45 |
| Gain | 39.1 | 38.6 | 39.1 | 0.42 | 0.59 | 0.45 |

$^{ab}$Means within the same row with different superscripts differ, P < 0.07.
Contrast 1 = Control (Treatment 1) versus Treatments 2 and 3
Contrast 2 = Treatment 2 versus Treatment 3 (Formulation C)

TABLE 32

Ruminal measurements for steers fed no yeast (Control/Treatment 1), Treatment 2, and Treatment 3 (Formulation C)

|  | Treatment | | | | Contrast, P< | |
|---|---|---|---|---|---|---|
| Measurement | 1 | 2 | 3(Form C) | SEM | 1 | 2 |
| Rumen pH | 6.58 | 6.51 | 6.65 | 0.10 | 0.23 | 0.65 |
| Rumen NH$_3$, mg N/dL | 9.8 | 12.7 | 13.3 | 1.6072 | 0.33 | 0.25 |
| Acetate, mM | 52.2 | 52.9 | 51.0 | 3.57 | 0.72 | 0.90 |
| Propionate, mM | 19.2 | 19.4 | 17.8 | 2.11 | 0.39 | 0.95 |
| Isobutyrate, mM | 0.55 | 0.62 | 0.62 | 0.05 | 0.75 | 0.31 |
| Butyrate, mM | 8.99 | 8.27 | 7.41 | 1.62 | 0.35 | 0.73 |
| Isovalerate, mM | 0.88 | 1.52 | 1.04 | 0.34 | 0.53 | 0.17 |
| Valerate, mM | 2.62 | 1.97 | 1.94 | 0.70 | 0.52 | 0.47 |
| Total VFA, mM | 84.4 | 84.6 | 79.8 | 7.18 | 0.48 | 0.99 |
| Acetate, Molar % | 61.9 | 62.6 | 64.0 | 2.10 | 0.28 | 0.80 |
| Propionate, Molar % | 23.2 | 23.0 | 22.3 | 2.00 | 0.65 | 0.94 |
| Isobutyrate, Molar % | 0.68 | 0.75 | 0.78 | 0.012 | 0.63 | 0.51 |
| Butyrate, Molar % | 10.2 | 9.63 | 9.24 | 1.02 | 0.45 | 0.68 |
| Isovalerate, Molar % | 1.12 | 1.79 | 1.29 | 0.36 | 0.61 | 0.22 |
| Valerate, Molar % | 2.97 | 2.26 | 2.40 | 0.58 | 0.65 | 0.34 |
| Acetate/propionate | 2.75 | 2.92 | 2.99 | 0.41 | 0.61 | 0.71 |
| Blood urea nitrogen, mg/dL | 12.2 | 11.9 | 12.8 | 1.35 | 0.68 | 0.87 |

Contrast 1 = Control (Treatment 1) versus Treatments 2 and 3
Contrast 2 = Treatment 2 versus Treatment 3 (Formulation C)

TABLE 33

Ruminal measurements for steers fed no yeast (Control/Treatment 1), Treatment 2, and Treatment 3 (Formulation C)

|  | Treatment | | | | Contrast, P< | |
|---|---|---|---|---|---|---|
| Microbial Community | 1 | 2 | 3 | SEM | 1 | 2 |
| Bacteria, log$_{10}$ CFU/ml | 10.21$^b$ | 10.39$^{ab}$ | 10.70$^a$ | 0.50 | 0.02 | 0.51 |
| Archaea, log$_{10}$ CFU/ml | 7.46$^{xy}$ | 7.41$^y$ | 7.67$^x$ | 0.12 | 0.08 | 0.77 |
| Entodinium, log$_{10}$ CFU/ml | 2.92 | 2.98 | 2.95 | 0.07 | 0.98 | 0.49 |
| Fungi, log$_{10}$ CFU/ml | 6.47 | 6.49 | 6.68 | 0.18 | 0.29 | 0.95 |
| Neocallimastigacaea, log$_{10}$ CFU/ml | 3.17 | 3.21 | 3.39 | 0.13 | 0.18 | 0.75 |
| Protozoa, log$_{10}$ CFU/ml | 3.48$^c$ | 3.88$^a$ | 3.64$^b$ | 0.15 | 0.63 | 0.02 |
| Saccharomyces, log$_{10}$ CFU/ml | 3.69 | 3.82 | 3.78 | 0.09 | 0.75 | 0.24 |
| Bovine, log$_{10}$ CFU/ml | 7.90 | 7.88 | 8.14 | 0.21 | 0.28 | 0.94 |

$^{ab}$Means within the same row with different superscripts differ, P < 0.05.
$^{xy}$Means within the same row with different superscripts differ, P < 0.08.
Contrast 1 = Control (Treatment 1) versus Treatments 2 and 3
Contrast 2 = Treatment 2 versus Treatment 3 (Formulation C)

Upon examination of the data shown in Tables 27-32, some complications in the study/trial were discovered. The calves had been subjected to an earlier trial that had a carry-over effect on this trial. The allotment to treatment in this trial did not stratify animals according to the earlier trial. The treatment in the previous trial significantly (P<0.05) influenced ruminal microbial composition and animal performance. Moreover, the treatment in the previous trial interacted with treatment in this trial such that the effect of previous treatment upon the results of this trial was not the same for all treatments. Plots of the data reveled outliers (grater than 3 standard deviation from the mean) in all significant response variables, providing nose for the analyses. Plots of weight over the course of the trial indicated that ADG was declining after day 50.

Based on these findings, an analysis was executed on data excluding outliers and accounting for the impact of the previous treatment, through employment of cofactors. The model for this analysis was:

Y=initial body weight+initial body height+treatment+ rep+treatment*rep+previous treatment+previous treatment*treatment+previous treatment*rep+ previous treatment*treatment*rep.

Also, since the growth of the animals over the time of the trial began to decline after day 50, growth parameters were evaluated for the first 50 days of the trial (designated as $1^{st}$ period) and after 50 days (designated as $2^{nd}$ period). The Least Square Means for this analysis is presented in FIGS. 10-21.

Figure 10:
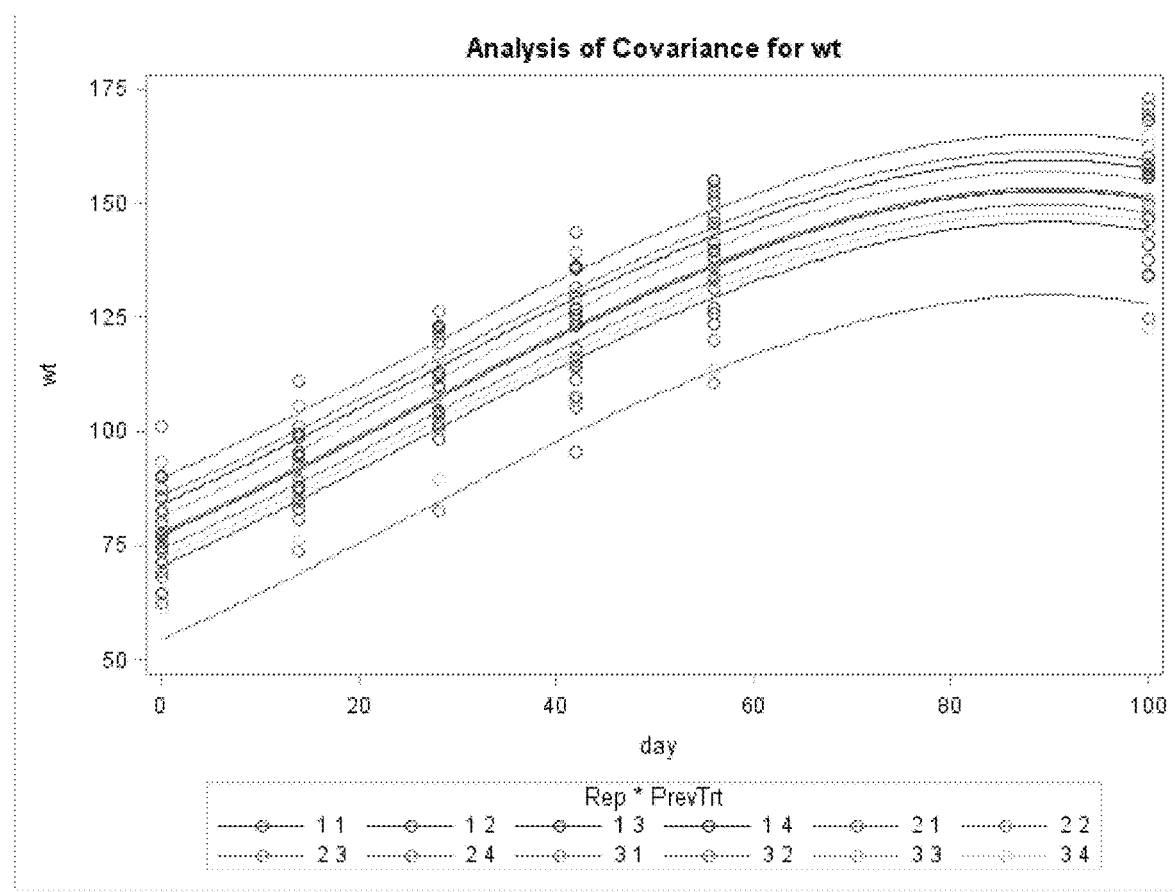
FIG. 10 is a graphical view of weight gain over the course of a calf trial delivering feed additive treatments, including a formulation of yeast and cobalt lactate, according to one or more embodiments of the invention.
Figure 11:
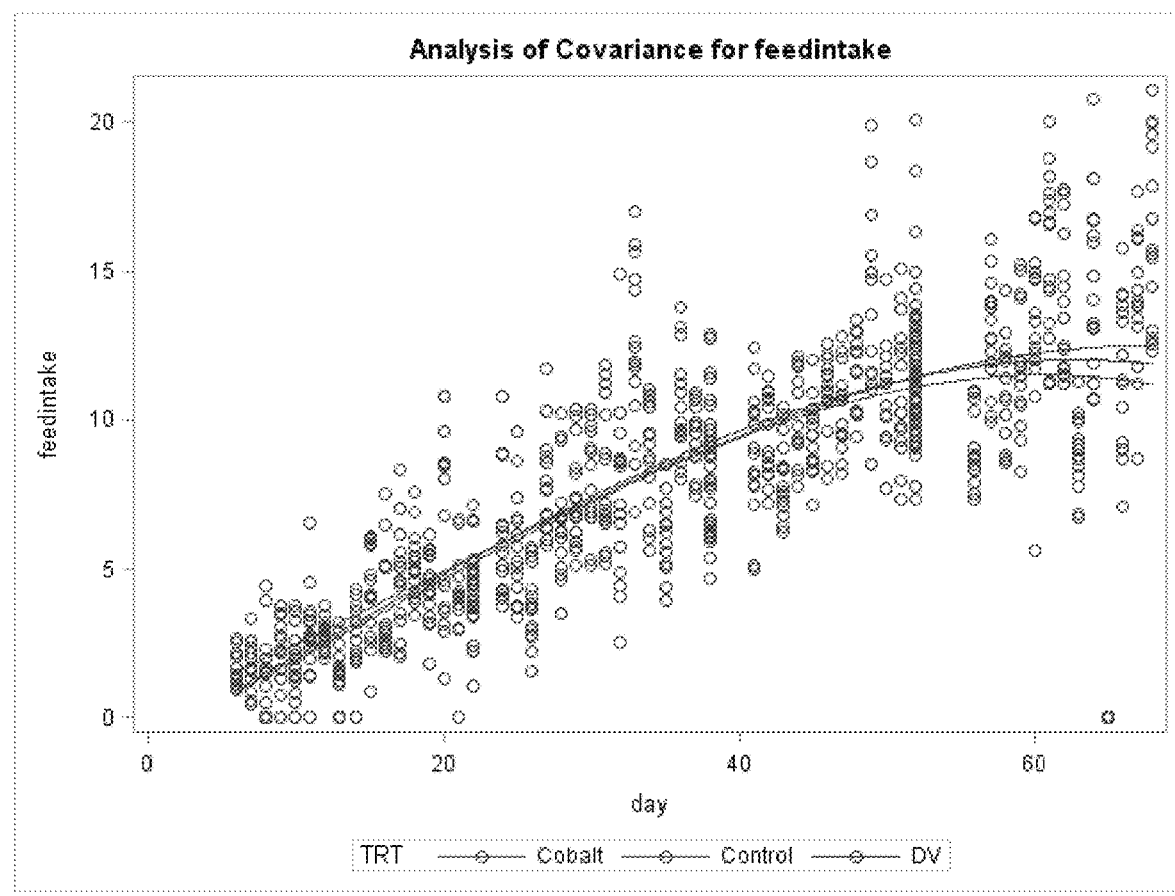
FIG. 11 is a graphical view of hay intake over the course of the calf trial, according to one or more embodiments of the invention.

FIG. 10 shows animal weight gain over the course of the trial. FIG. 11 shows hay intake over the course of the trial. The treatment designations in FIG. 11 are as follows: Cobalt=Treatment 3 (Formulation C), Control=Treatment 1, DV=Treatment 2. FIG. 10 shows that there was a change observed near or around day 50 and the weight gain dropped as the weight of the animals started to level off across all of the treatments. FIG. 11 shows that the hay intake of the animals matched with the trend observed for weight. These two figures indicate that there were two phases observed over the course of the trial.

Figure 12:
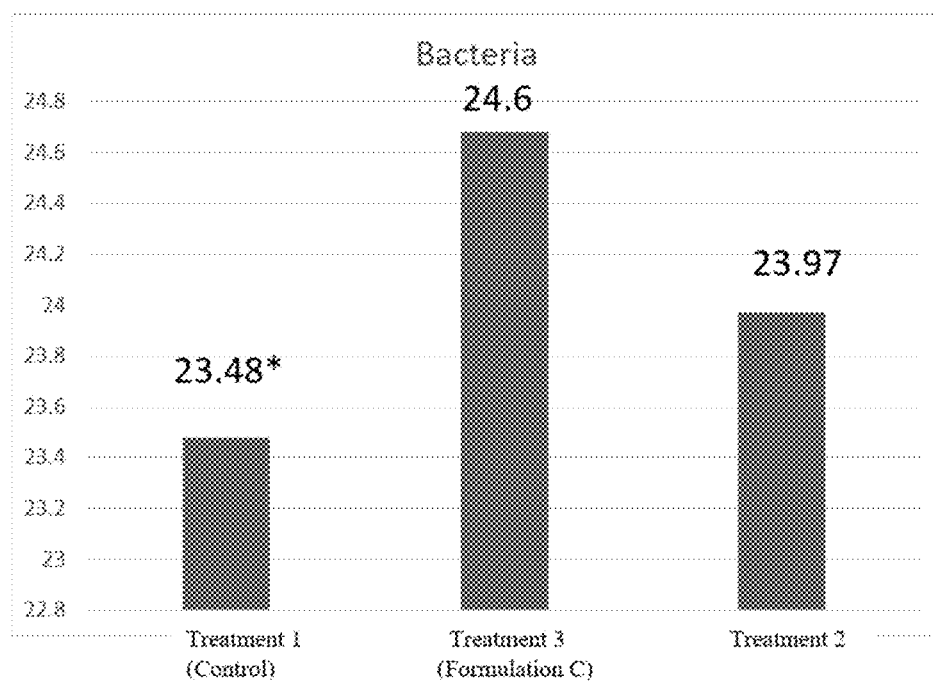
FIG. 12 is a graphical view of the effect of various treatments on ruminal bacteria in the calf trial, according to one or more embodiments of the invention.
Figure 13:
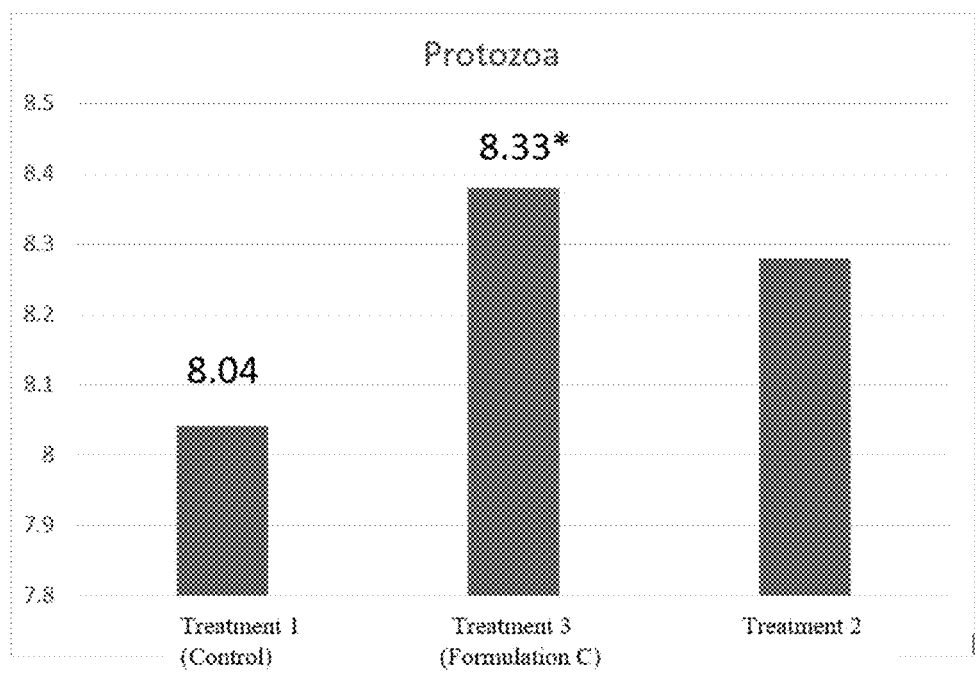
FIG. 13 is a graphical view of the effect of various treatments on ruminal protozoa in the calf trial, according to one or more embodiments of the invention.

FIG. 12 shows effect of treatment on ruminal bacteria (t test, P=0.038). FIG. 13 shows effect of treatment on ruminal protozoa (t test, P<0.01).

Figure 14:
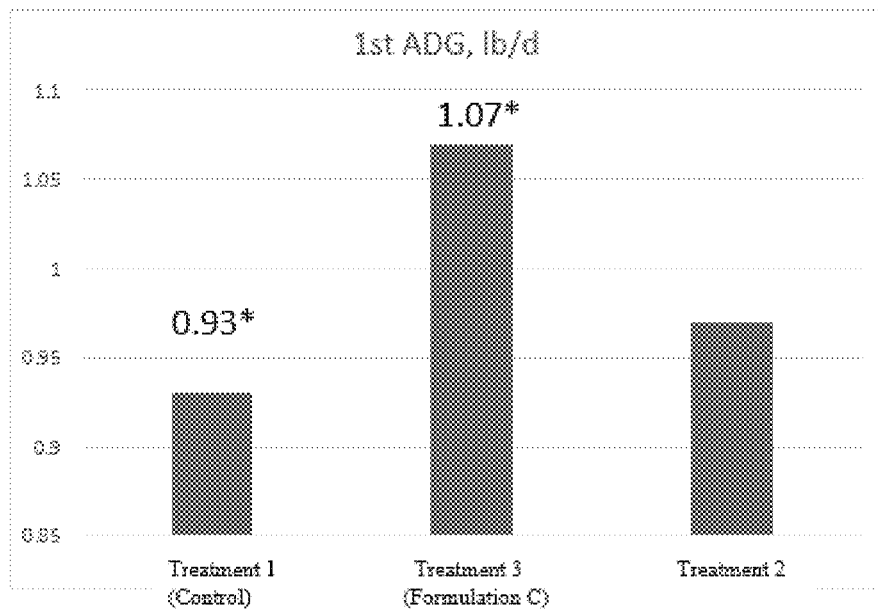
FIG. 14 is a graphical view of the effect of various treatments on average daily grains (ADG) for the first period in the calf trial, according to one or more embodiments of the invention.
Figure 15:
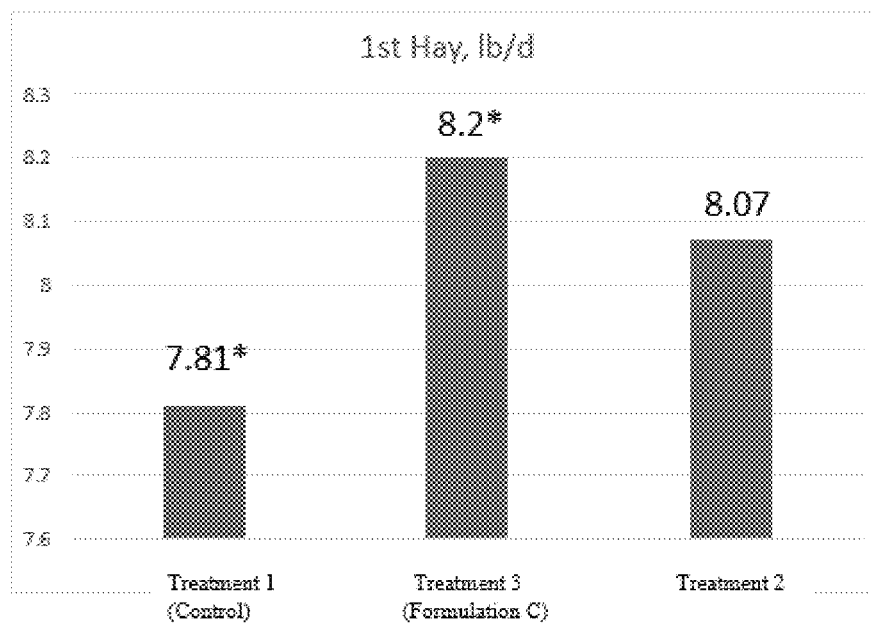
FIG. 15 is a graphical view of the effect of various treatments on hay intake for the first period in the calf trial, according to one or more embodiments of the invention.
Figure 16:
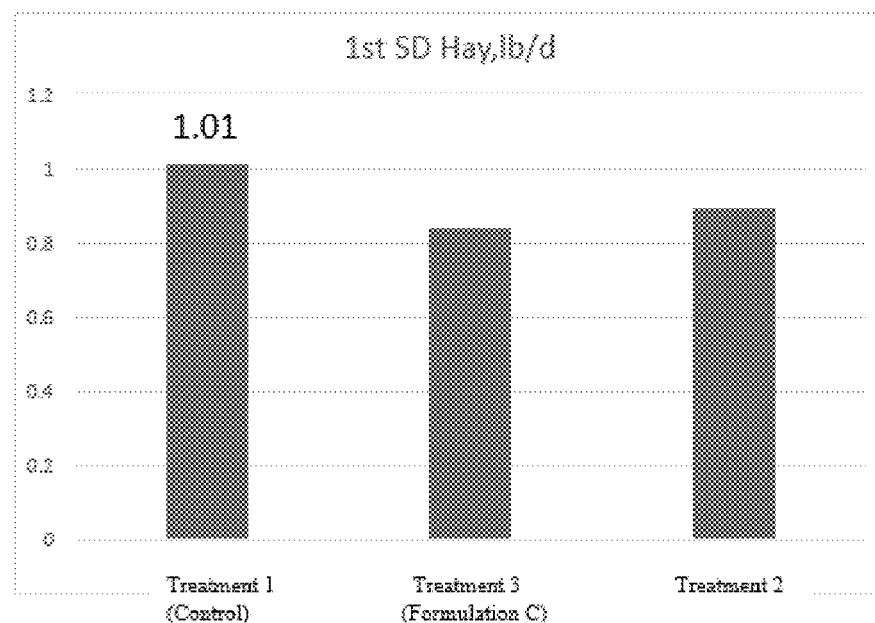
FIG. 16 is a graphical view of the effect of various treatments on day to day variation in feed intake in the calf trial, according to one or more embodiments of the invention.
Figure 17:
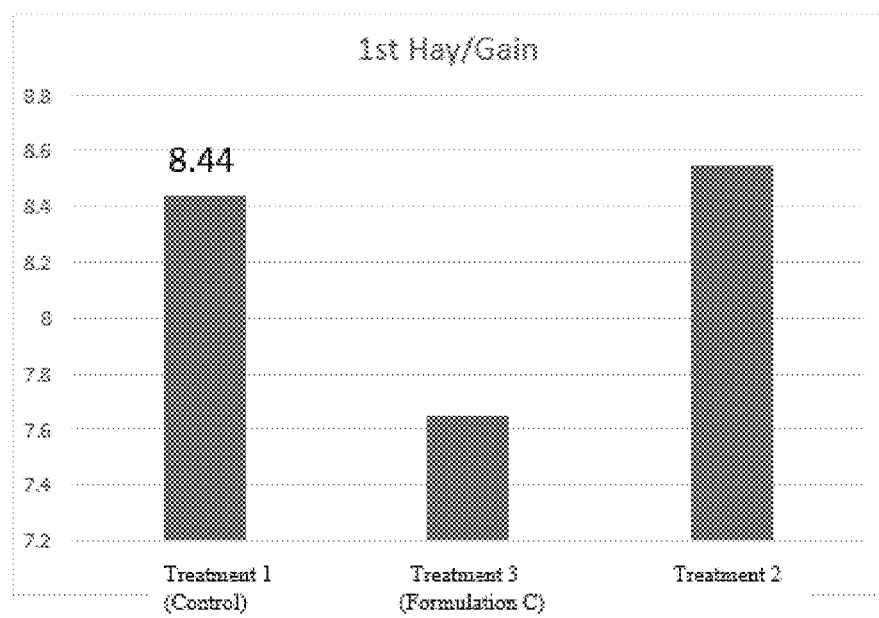
FIG. 17 is a graphical view of the effect of treatment on a hay to gain ratio in the calf trial, according to one or more embodiments of the invention.

FIG. 14 shows effect of treatment on ADG during $1^{st}$ period (t test, P=0.066). FIG. 15 shows effect of treatment on hay intake in the $1^{st}$ period (t test, P=0.07). FIG. 16 shows effect of treatment on day to day variation (SD=Standard Deviation) in feed intake in $1^{st}$ period. FIG. 17 shows effect of treatment on hay/gain ratio in the $1^{st}$ period.

Figure 18:
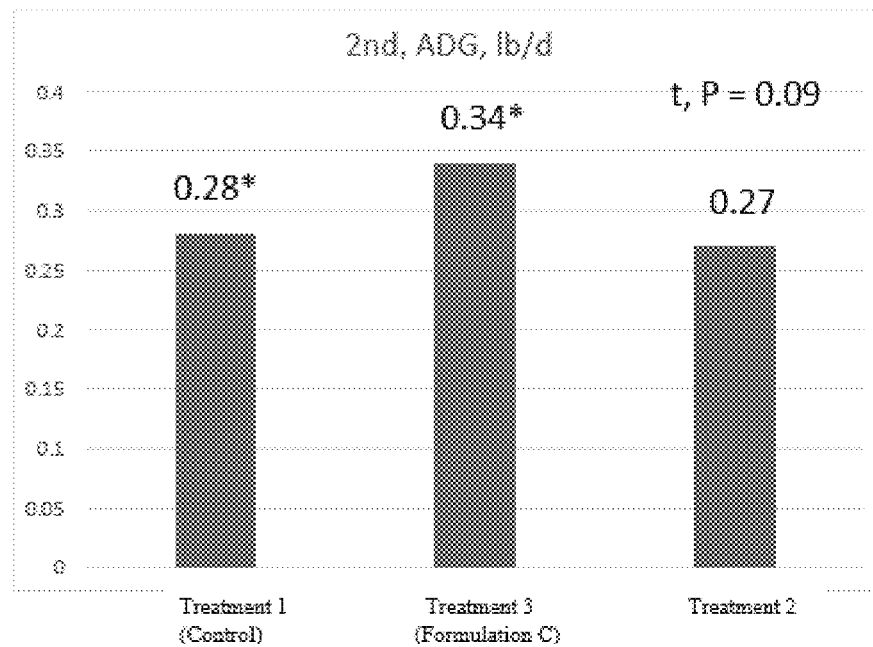
FIG. 18 is a graphical view of the effect of treatment on ADG during the second period in the calf trial, according to one or more embodiments of the invention.
Figure 19:
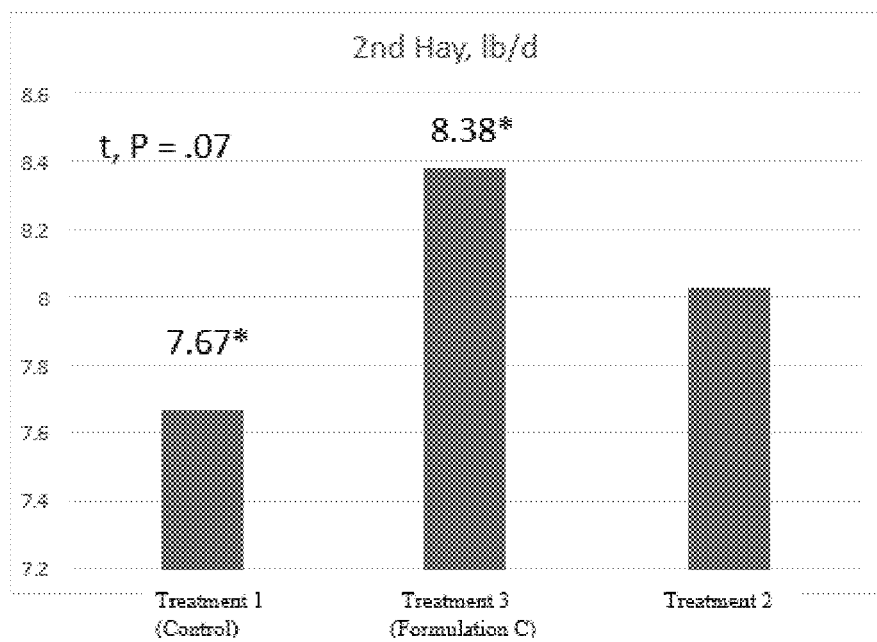
FIG. 19 is a graphical view of the effect of treatment on hay intake for the second period in the calf trial, according to one or more embodiments of the invention.
Figure 20:
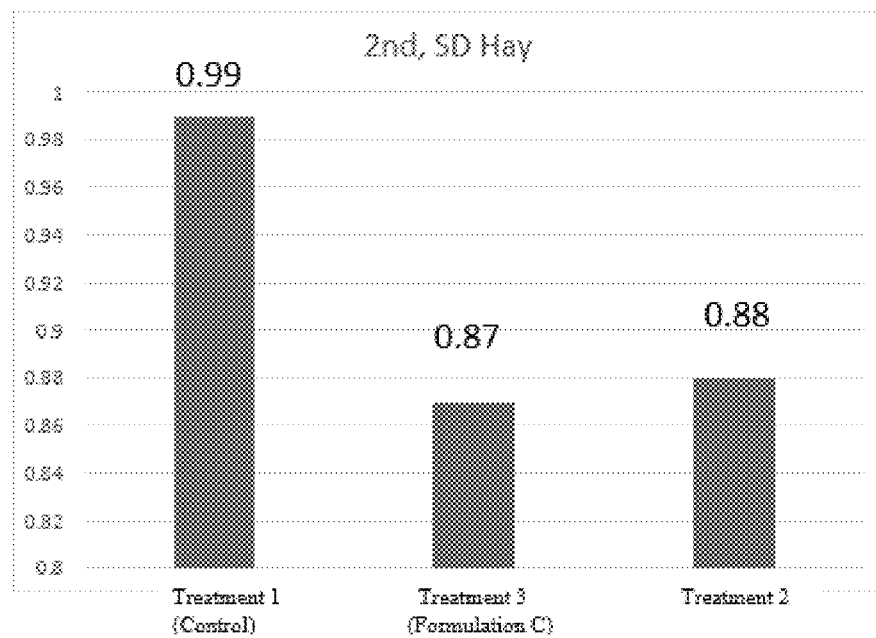
FIG. 20 is a graphical view of the effect of treatment on day to day variation in feed intake in the calf trial, according to one or more embodiments of the invention.
Figure 21:
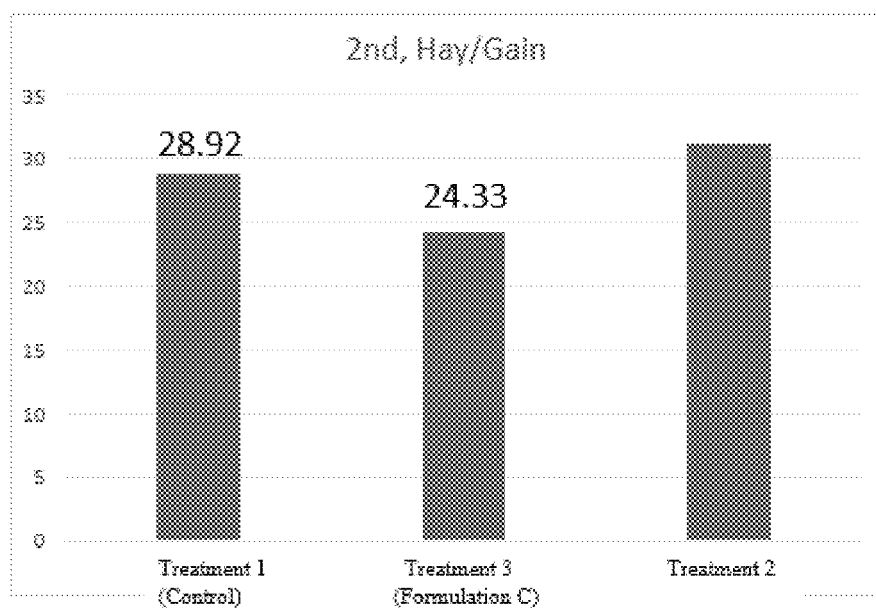
FIG. 21 is a graphical view of the effect of treatment on a hay to gain ratio in the calf trial, according to one or more embodiments of the invention.

FIG. 18 shows effect of treatment on ADG during the $2^{nd}$ period (t test, P=0.09). FIG. 19 shows effect of treatment on hay intake in the $2^{nd}$ period (t test, P=0.07). FIG. 20 shows effect of treatment on day to day variation (SD=Standard Deviation) in hay intake in the $2^{nd}$ period. FIG. 21 shows effect of treatment on hay/gain ratio in the $2^{nd}$ period.

Conclusions taken from analyzing the data, including Tables 27-32 and FIGS. 10-21, include: Treatment 3 (Formulation C) increases ruminal bacteria and protozoa, indicating early rumen development and ability to digest fiber. The early rumen development aids the calf to eat more hay and do it more consistently from day-to-day. Greater nutrient intake enables increased growth in terms of weight and frame.

Feeding the calves Treatment 3 can reduce feed cost by allowing for more forage in the ration to achieve greater results compared to Treatment 2, due to increasing ruminal bacteria and protozoa concentrations. Such increased concentrations can indicate earlier rumen function allowing the animals to each more forage earlier in life thereby increasing their rate of growth early in life.

The scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto.

Various examples have been described. These and other examples are within the scope of the following claims.

What is claimed is:

1. A method of improving performance of a ruminant, the method comprising:
administering to a ruminant a feed additive composition comprising about 1 wt. % to about 3 wt. % of a cobalt compound, about 0.5 wt. % to about 15 wt. % of one or more essential oils selected from the group consisting of thyme, cinnamon, and oregano, and about 48 wt. % to about 98 wt. % of a yeast component, wherein a ratio of the yeast component to the cobalt compound is between about 140:1 and 13:1, and wherein the feed additive composition contributes to at least one of: increased milk production of dairy cows, increased feed efficiency, increased digestibility, and an improvement in early rumen development, as compared to if the ruminant was not administered the feed additive composition.

2. The method of claim 1, wherein the ratio of the yeast component to the cobalt compound is between about 50:1 and 25:1.

3. The method of claim 1, wherein the ratio of the yeast component to cobalt is 65:1.

4. The method of claim 1, wherein administering to a ruminant a feed additive composition includes providing a daily dose to the ruminant of the feed additive composition containing between about 75 and about 225 milligrams of the cobalt compound.

5. The method of claim 4, wherein the feed additive composition contains between about 75 and about 150 milligrams of the cobalt compound.

6. The method of claim 1, wherein administering to a ruminant a feed additive composition includes providing a daily dose to the ruminant of the feed additive composition containing between about 3 and about 10 grams of the yeast component.

7. The method of claim 6, wherein the feed additive composition contains between about 3 and about 7 grams of the yeast component.

8. The method of claim 1, wherein the cobalt compound is at least one of a cobalt lactate compound, a cobalt acetate compound, a cobalt formate compound, a cobalt oxalate compound, a cobalt propionate compound, a cobalt butyrate compound, a cobalt gluconate compound, a cobalt fumarate compound, a cobalt valerate compound, a cobalt 2-ethylcaproate compound, a cobalt citrate compound, a cobalt sorbate compound, a cobalt benzoate compound, a cobalt enanthate compound, a cobalt dioctanoate compound, a cobalt pelargonate compound, a cobalt decanoate compound, a cobalt laurate compound, a cobalt myristate compound, a cobalt palmitate compound, a cobalt margarate compound, a cobalt stearate compound, a cobalt icosanoate compound, a cobalt ethylenediamine tetraacetate (EDTA) compound, a cobalt ethylene diamine compound, a cobalt bromide compound, a cobalt chloride compound, a cobalt fluoride compound, a cobalt carbonate compound, a cobalt hydroxide compound, a cobalt nitrate compound, a cobalt oxide compound, a cobalt phosphate compound, a cobalt sulfate compound, a cobalt malate compound, a cobalt tartrate compound, and any hydrate thereof.

9. The method of claim 1, wherein the yeast component is a yeast, a yeast culture, a yeast extract, a yeast product, a fermented yeast, and any combination thereof.

10. The method of claim 1, wherein the essential oil is combined with an emulsifier to form an emulsion in which an average particle size of the at least one essential oil in the emulsion is about 25 microns or less.

11. The method of claim 10, wherein the emulsifier includes larch arabinogalactan.

* * * * *